US009764012B2

(12) United States Patent
Daftarian et al.

(10) Patent No.: US 9,764,012 B2
(45) Date of Patent: Sep. 19, 2017

(54) VACCINE COMPOSITIONS AND METHODS OF USE THEREOF

(75) Inventors: Pirouz M. Daftarian, Miami, FL (US); Paolo Serafini, Miami Shores, FL (US); Vance Paul Lemmon, Miami, FL (US); Angel Kaifer, Coral Gables, FL (US); Victor Perez, Pinecrest, FL (US); Wei Li, Miami, FL (US); Bonnie Beth Blomberg, Coral Gables, FL (US)

(73) Assignee: UNIVERSITY OF MIAMI, Miami, FL (US)

( * ) Notice: Subject to any disclaimer, the term of this patent is extended or adjusted under 35 U.S.C. 154(b) by 371 days.

(21) Appl. No.: 13/262,285

(22) PCT Filed: Apr. 1, 2010

(86) PCT No.: PCT/US2010/029694
§ 371 (c)(1),
(2), (4) Date: Dec. 19, 2011

(87) PCT Pub. No.: WO2010/115046
PCT Pub. Date: Oct. 7, 2010

(65) Prior Publication Data
US 2012/0093761 A1 Apr. 19, 2012

Related U.S. Application Data

(60) Provisional application No. 61/165,732, filed on Apr. 1, 2009.

(51) Int. Cl.
*A61K 39/395* (2006.01)
*A61K 39/00* (2006.01)
*A61K 39/145* (2006.01)
*C08G 83/00* (2006.01)
*A61K 39/12* (2006.01)

(52) U.S. Cl.
CPC .......... *A61K 39/0011* (2013.01); *A61K 39/12* (2013.01); *A61K 39/145* (2013.01); *C08G 83/006* (2013.01); *A61K 2039/53* (2013.01); *A61K 2039/55516* (2013.01); *A61K 2039/55555* (2013.01); *A61K 2039/645* (2013.01); *C12N 2760/16022* (2013.01); *C12N 2760/16034* (2013.01); *G01N 2333/70539* (2013.01)

(58) Field of Classification Search
None
See application file for complete search history.

(56) References Cited

U.S. PATENT DOCUMENTS

| | | | |
|---|---|---|---|
| 6,632,435 B1 | 10/2003 | Diamond | |
| 2003/0232968 A1* | 12/2003 | Li et al. | 530/350 |
| 2004/0241842 A1 | 12/2004 | Boyd | |
| 2004/0258660 A1 | 12/2004 | Klysner et al. | |
| 2005/0169900 A1 | 8/2005 | Gansbacher | |
| 2005/0180947 A1 | 8/2005 | Pederson et al. | |
| 2005/0208120 A1 | 9/2005 | Albani | |
| 2005/0232948 A1 | 10/2005 | Hennessy et al. | |
| 2006/0035291 A1 | 2/2006 | Itoh et al. | |
| 2007/0135373 A1 | 6/2007 | Li et al. | |
| 2008/0032921 A1 | 2/2008 | Alexander et al. | |

(Continued)

FOREIGN PATENT DOCUMENTS

AU  WO2008151389  * 12/2008
CN  1323217  11/2001

(Continued)

OTHER PUBLICATIONS

Boas et al. Dendrimers in Drug Research. Chem Soc Rev. 2004, 33(1):43-63.
Graham, New Approaches to Vaccine Adjuvants; Inhibiting the Inhibitor. PLoS Med 2006, vol. 3(1).
Belot, et al. Synthesis of Two Linear PADRE Conjugates Bearing a Deca- or Pentadecasaccharide B Epitope as Potential Synthetic Vaccines against Shigella Flexneri Serotype 2a Infection. Chemistry—A European Journal 2005, 11(5): 1625-1635.
Alexander, et al. Linear PADRE T Helper Epitope and Carbohydrate B Cell Epitope Conjugates Induce Specific High Titer IgG Antibody Responses. J. Immunol. 2000, 164; 1625-1633.
Alexander, et al. Development of High Potency University DR-Restricted Helper Epitopes by Modification of High Affinity DR-Bocking Peptides. Immunity 1994, 1:751-761.

(Continued)

*Primary Examiner* — Yunsoo Kim
(74) *Attorney, Agent, or Firm* — Fox Rothschild LLP

(57) ABSTRACT

Nanoparticle-based vaccines, compositions, kits and methods are used for the effective delivery of one or more antigens in vivo for vaccination and antibody (e.g., monoclonal antibody) production, and for the effective delivery of peptides, proteins, siRNA, RNA or DNA to PAPCs or MHC class II positive cells (e.g. tumor cells). Antigens may be, for example, DNA that results in expression of the gene of interest and induction of a robust and specific immune response to the expressed protein in a subject (e.g., mammal). Antigens may also be immunogenic peptides or polypeptides that are processed and presented. In one embodiment, a nanoparticle-based method to deliver antigens in vivo as described herein includes injection of a vaccine composed of a DNA encoding at least one antigen, or at least one antigenic peptide or polypeptide conjugated to a charged dendrimer (e.g., PADRE-derivatized dendrimer) that is also conjugated to a T helper epitope (e.g., PADRE). Negatively-charged plasmids bind naturally to a positively-charged PADRE-dendrimer, while peptide or polypeptide antigens can be chemically linked to the PADRE-dendrimer if they are not negatively-charged. Alternatively, negatively-charged dendrimers may be used. The compositions, kits, vaccines and methods described herein have both prophylactic and treatment applications, i.e., can be used as a prophylactic to prevent onset of a disease or condition in a subject, as well as to treat a subject having a disease or condition. A vaccine as described herein can be used to mount an immune response against any infectious pathogen or cancer.

14 Claims, 18 Drawing Sheets

(56) References Cited

U.S. PATENT DOCUMENTS

2008/0219992 A1 9/2008 Alving et al.
2008/0268457 A1 10/2008 Khvorova et al.
2009/0123467 A1* 5/2009 Bedi ................... A61K 47/484
424/134.1

FOREIGN PATENT DOCUMENTS

| CN | 1630531 | 6/2005 |
|---|---|---|
| CN | 1809379 | 7/2006 |
| CN | 101506266 | 8/2009 |
| JP | 09505559 | 6/1997 |
| WO | 9843677 | 10/1998 |
| WO | 2007089607 | 8/2007 |
| WO | 2008113119 | 9/2008 |
| WO | 2010115046 | 10/2010 |

OTHER PUBLICATIONS

International Search Report and Written Opinion issued in International Application No. PCT/US10/29694 dated Sep. 17, 2010 (20 pages).
Agadjanyan et al., "Prototype Alzheimer's Disease vaccine using the immunodominant B cell epitope from beta-amyloid and promiscuous T cell epitope pan HLA DR-binding peptide", Journal of Immunology (Feb. 2005) 174(3): 1580-1586. (abstract only).
Daftarian et al., "Peptide-conjugated PAMAM dendrimer as a universal DNA vaccine platform to target antigen-presenting cells", Cancer Research (Dec. 2011) 71(24): 7452-7462.
European Search Report dated May 21, 2013 in EP Application No. 10778304.5. (19 pages).
First Office Action dated Apr. 11, 2013 in Chinese Application No. 201080029414.7. (24 pages).
International Search Report and the Written Opinion of the ISA dated Sep. 21, 2010 in PCT Application No. PCT/US10/35355, international filing date May 19, 2010. (28 pages).
Heegaard et al., "Dendrimers for vaccines and immunostimulatory uses. A review", Biconjugate Chemistry (Nov. 2009) 21(3): 1043-1802.
Kim et al., "Enhancement of DNA vaccine potency through coadministration of CIITA DNA with DNA vaccines via gene gun", Journal of Immunology (May 2008) 180(10): 7019-7027. (abstract only).
Mansour et al., "Therapy of established B16-F10 melanoma tumors by a single vaccination of CTL/T helper peptides in VacciMax®", Journal of Translational Medicine (Apr. 2007) 5(1): 20. (abstract only).
Niederhafner et al., "Glycopeptide dendrimers, part III—a review: Use of glycopetide dendrimers in immunotherapy and diagnosis of cancer and viral diseases", Journal of Peptide Science (May 2008) 14(5): 556-587.
Sastry et al., "Improving the sensitivity of the ELISPOT analyses of antigen-specific cellular immune responses in Rhesus Macaques", Methods in Molecular Biology (2007) 302: 153-165.
Lo-Man et al., "A fully synthetic therapeutic vaccine candidate targeting carcinoma-associated Tn carbohydrate antigen induces tumor-specific antibodies in nonhuman primates", Cancer Research (2004) 64(14): 4987-4994.
Niederhafner et al., "Glycopeptide dendrimers. Part I", Journal of Peptide Science (May 2008) 14: 2-43.
Niederhafner et al., "Glycopeptide dendrimers. Part II", Journal of Peptide Science (May 2008) 14: 44-65.
Canadian Office Action dated Nov. 25, 2014 in Canadian Application No. 2,762,586. (4 pages).
Seabrook et al., "Boosting with intranasal dendrimeric Abeta 1-15 but not Aβ 1-15 peptide leads to an effective immune response following a single injection of Aβ 1-40/42 in APP-tg mice", Journal of Neuroinflammation (2006) 3:14.
European Examination Report dated Mar. 9, 2016 in corresponding Application No. EP 10759434.3.
Lo-Man R et al: "Anti-tumor immunity provided by a synthetic multiple antigenic glycopeptide displaying a tri-Tn glycotope", The Journal of Immunology, The American Association of Immunologists, vol. 166, No. 4, Feb. 15, 2001, pp. 2849-2854.
Tam J P et al: "Vaccine engineering: enhancement of iimmunogenicity of synthetic peptide vaccines related to hepatitis in chemically defined models consisting of t- and b-cell epitopes", proceedings of the national academy of sciences—PNAS, National Academy of Sciences, vol. 86, No. 23, Jan. 1, 1989, pp. 9084-9088.
Eichman J D et al: "The use of PAMAM dendrimers in the efficient transfer of genetic material into cells", Pharmaceutical Science and Technology Today Jul. 1, 2000, vol. 3, No. 7, Jul. 1, 2000, pp. 232-245.
Shukla Rameshwer et al: "Tumor angiogenic vasculature targeting with PAMAM dendrimer—RGD conjugates.", Chemical Communications (Cambridge, England) Dec. 14, 2005, No. 46, pp. 5739-5741.
Seabrook et al: "Dendrimeric Abetal-15 is an effective immunogen in wildtype and APP-tg mice", Neurobiology of Aging, vol. 28, No. 6, Apr. 19, 2007 (Apr. 19, 2007), pp. 813-823.
Vlasov G P et al: "Lysine dendrimers and their starburst polymer derivatives: possible application for DNA compaction and in vitro delivery of genetic constructs", Russian Journal of Bioorganic Chemistry, vol. 30, No. 1, Jan. 1, 2004, pp. 12-20.
Fu et al: "Dendrimer/DNA complexes encapsulated in a water soluble polymer and supported on fast degrading star poly(dl-lactide) for localized gene delivery", Journal of Controlled Release, vol. 124, No. 3, Nov. 16, 2007, pp. 181-188.
P. Daftarian et al: "Peptide-Conjugated PAMAM Dendrimer as a Universal DNA Vaccine Platform to Target Antigen-Presenting Cells", Cancer Research, vol. 71, No. 24, Dec. 15, 2011, pp. 7452-7462.
Wijesekara et al.: "miR-33a Modulates ABCA1 Expression, Cholesterol Accumulation, and Insulin Secretion in Pancreatic Islets", Diabetes, vol. 61, No. 3, pp. 653-658,published on Mar. 31, 2012.
Yancey et al.: "Cellular Cholesterol Efflux Mediated by Cyclodextrins", The Journal of Biological Chemistry, vol. 271, No. 27, pp. 16026-16034, published on Jul. 5, 1996.
Tang et al.: "Diabetes Reduces the Cholesterol Exporter ABCA1 in Mouse Macrophages and Kidneys", Journal of Lipid Research, vol. 51, pp. 1719-1728, published on Dec. 31, 2010.

\* cited by examiner

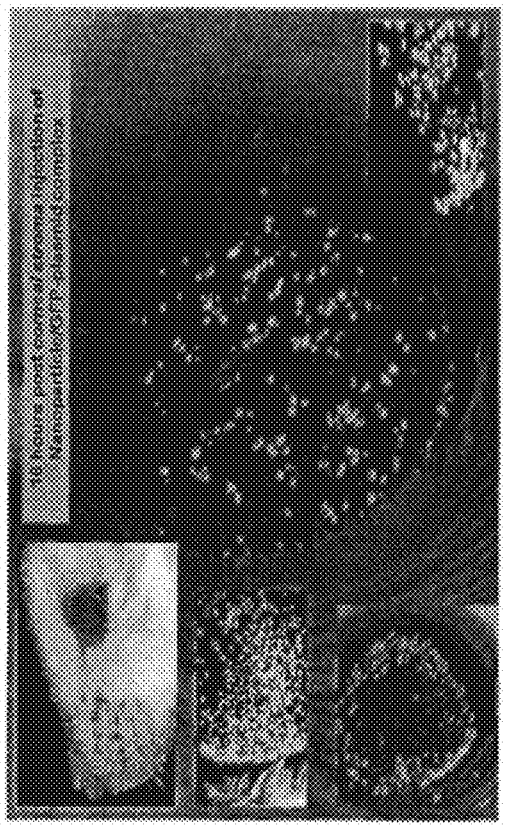
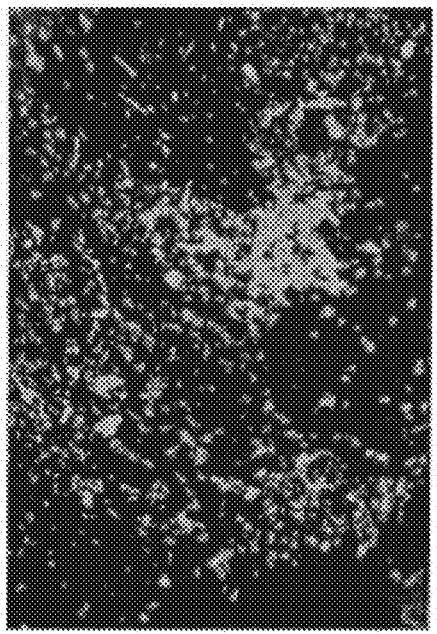
FIG. 3

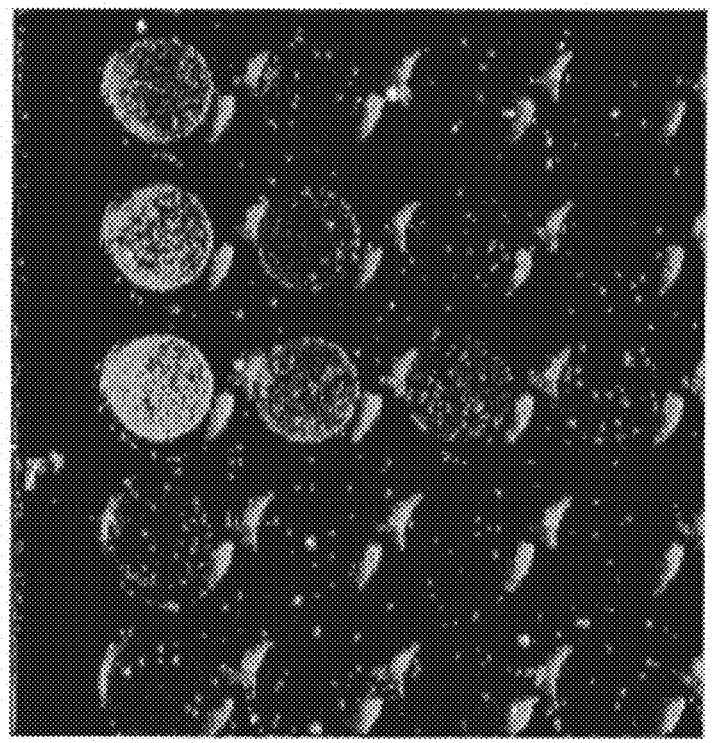
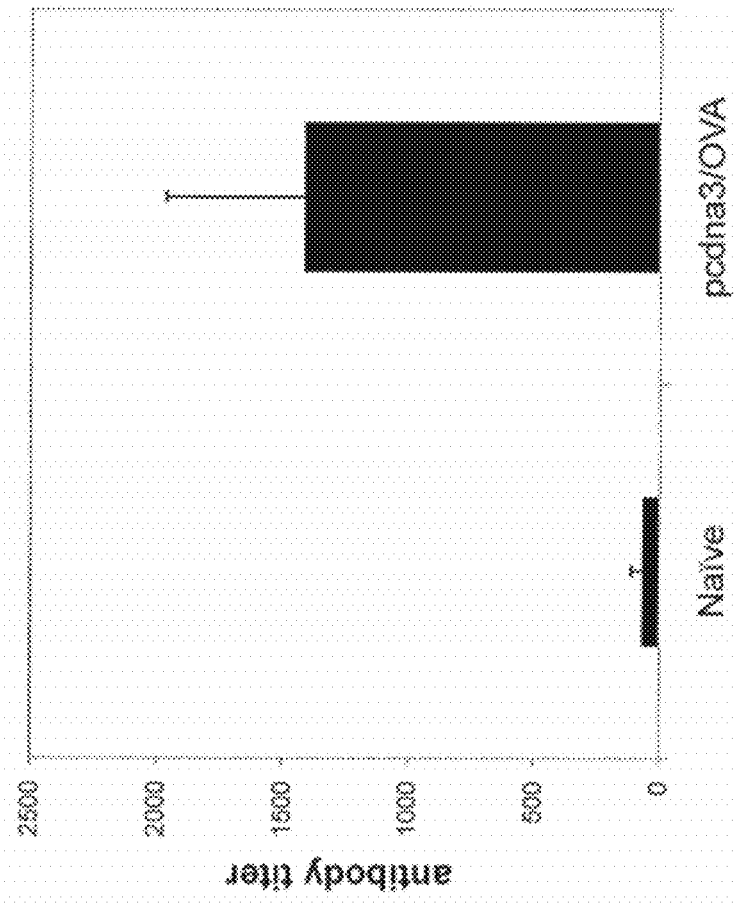
FIG. 4

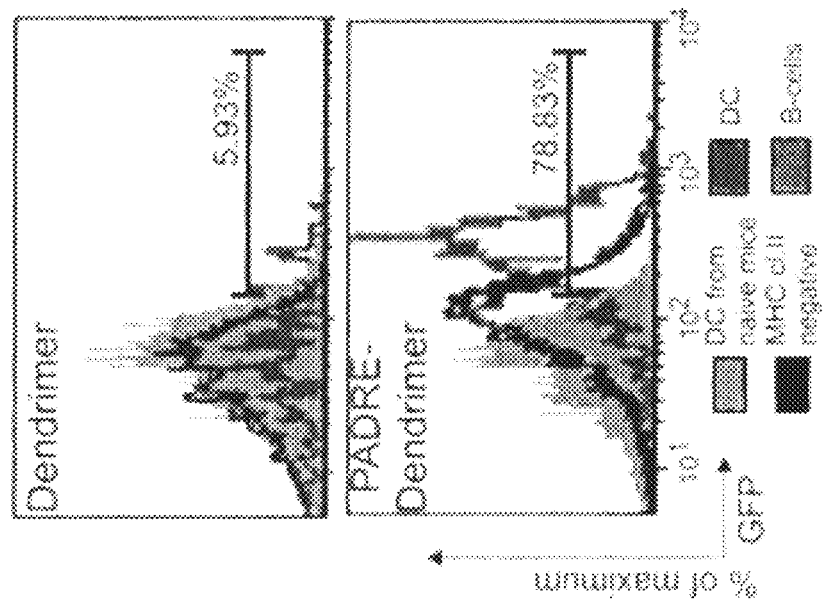
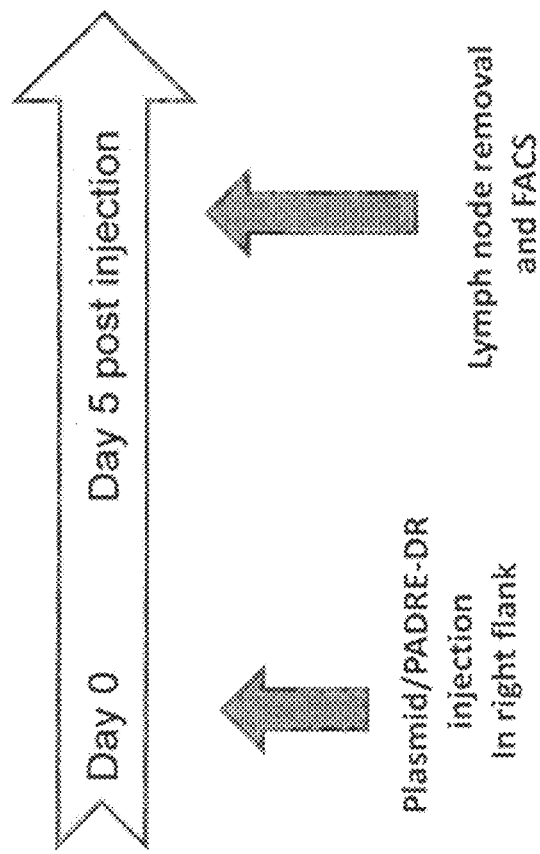
FIG. 8

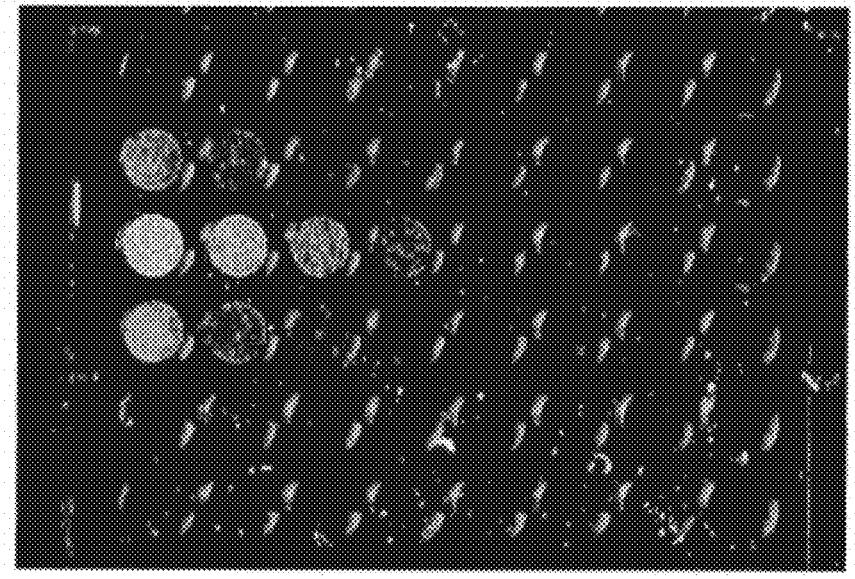
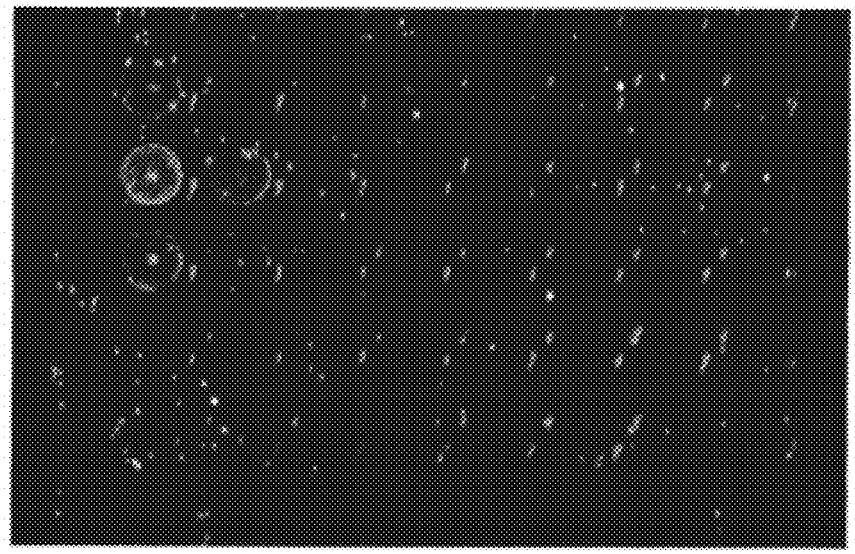
FIG. 16

VACCINE COMPOSITIONS AND METHODS OF USE THEREOF

CROSS REFERENCE TO RELATED APPLICATIONS

The present application is a §371 national phase entry of International Application No. PCT/US2010/29694, filed Apr. 1, 2010, which claims priority to U.S. provisional patent application No. 61/165,732 filed Apr. 1, 2009, the entire contents of which are incorporated herein by reference.

SEQUENCE LISTING

The instant application contains a Sequence Listing which has been submitted in ASCII format via EFS-Web and is hereby incorporated by reference in its entirety. Said ASCII copy, created on Dec. 16, 2011, is named 7230611.txt and is 9,635 bytes in size.

FIELD OF THE INVENTION

The invention relates generally to the fields of chemistry and immunology. More particularly, the invention relates to vaccines, compositions and methods for inducing an immune response in a subject.

BACKGROUND

The prevention of microbial infections and pathogenic processes via the use of vaccines is considered one of the most effective and desirable procedures to combat illness. Antigens or immunogens are introduced into an organism in a manner that stimulates an immune response in the host organism in advance of an infection or disease. Traditional vaccine strategies, however, have not been effective in mounting protection against many pathogens or cancers. Of more than 100 pathogens, only about 20 successful vaccines have been made by traditional vaccine strategies. Of those vaccines that induce a high cytotoxic T lymphocyte (CTL) response, some often show a modest objective response rate due to poor immunogenicity, immuno-avoidance mechanisms, and deceptive imprinting. Current methods of vaccine delivery have a modest success rate in terms of inducing protective immune responses because they do not induce robust "danger signals," they initiate inhibitory responses that act as feedback mechanisms, and they deliver antigens to nonprofessional antigen presenting cells (APCs). Current cancer vaccines, for example, even when mounting a high CTL response, show a modest (2.6%) objective response rate. They are associated with a number of disadvantages, including poor immunogenicity and immuno-avoidance mechanisms. Moreover, the most promising cancer vaccines (dendritic cell-based and G-vax-based), are extremely costly and preparation of these vaccines is very involved (e.g., requiring personalization and GMP manufacturing).

Genetic vaccination or genetic immunization, which involves the inoculation of genetic materials into mammalian hosts to produce antigens, is considered a possible approach for vaccines including cancer vaccines. The delivered mammalian expression vector encoding the antigen of interest results in in vivo expression and subsequently to the development of antigen-specific responses. In addition, genes are negatively-charged polymers, which cannot cross cell membranes and reach the cell nucleus, where they can express a protein of interest. Genetic vaccination offers a number of advantages, including generation of a full spectrum of native epitopes expressed in vivo, achievement of the native conformation of a protein compared with administration of recombinant protein expressed in vitro, induction of antibody and cellular immune responses, and elimination of the need for costly and commonly challenging steps for antigen production. Genetic vaccination, however, is associated with a number of disadvantages including breaking tolerance to self antigens, poor in vivo delivery of nucleic acids into the cell and nucleus, a lack of specificity for particular types of cells, and weak immune responses.

Other forms of vaccines are associated with drawbacks as well. For example, viral delivery of genes results in strong immune responses to viral vectors and is associated with safety concerns. Protein purification from bacteria and production of peptides for use as antigens is expensive and time consuming.

Currently, there are no cost-effective, efficacious forms of vaccines that target APCs to produce specific and robust immune responses with no or few side effects. There is thus a significant need for a vaccine that targets professional APCs and elicits a strong and specific cellular and antibody response and that is safe, cost-effective and easy to use.

SUMMARY

Described herein are nanoparticle-based compositions, kits and methods and platforms for delivering an antigen or a nucleic acid encoding an antigen to professional APCs (PAPCs) in vivo that result in a robust and specific immune response to the antigen. Also described herein are nanoparticle-based compositions, kits, methods and platforms for delivering siRNA to PAPCs, and for delivering nucleic acids, peptides or proteins to cells (e.g., MHC Class II expressing tumor cells). A major deficit of current vaccine strategies is that they induce suppressor cells including regulatory T cells. Targeted delivery of antigen to PAPCs is known to reduce or inhibit the activation of suppressor mechanisms, in particular, those of regulatory T cells. The composition, kits and methods involve the combined use of MHC targeting and immunogenic peptides (e.g., PADRE, HA) with charged (e.g., positively-charged) highly branched polymeric dendrimers (e.g., PAMAM and other dendrimers) as vehicles for the targeted delivery of nucleic acids, peptides or polypeptides to specific cells, giving rise to a new nanoparticle-based method for genetic or protein vaccination. Typical vaccines described herein include a charged (e.g., positively-charged) highly branched polymeric dendrimer conjugated to an MHC targeting and immunogenic peptide such as T helper peptide (e.g., an epitope such as the PADRE peptide or Influenza HA), at least one polypeptide antigen or a nucleic acid encoding the at least one antigen, and optionally Poly I-C. The positively-charged highly branched polymeric dendrimers described herein effectively bind negatively-charged biomolecules including DNA, RNA and others. Charged (e.g., positively-charged) highly branched polymeric dendrimers conjugated to a T helper peptide (e.g., an epitope such as the PADRE peptide or Influenza HA) provide vaccines with increased efficacy due to specific antigen delivery to PAPCs. In the experiments described herein, the first use of PADRE to target PAPCs via its binding to MHC class II molecules is shown. The experiments described herein describe effective use of two different targeting peptides, whose unique feature is to bind to the MHC class II. Thus, the vaccines, methods and compositions described herein encompass all MHC class II binding peptides. The vaccines, kits and compositions described herein provide for specific and efficient transfection of PAPCs in vivo, and built-in universal T helper activity universally that result in maturation of autologous PAPCs and hence robust and specific immune responses.

Dendrimers are an ideal DNA delivery candidate for they provide structural control over size and shape (cargo-space), are biocompatible (non-toxic and nonimmunogenic), have precise scaffolding properties, have a well-defined surface-modifiable functionality for specific targeting moieties, have the ability for cellular adhesion and endocytosis and delivery into the cytoplasm or nucleus, have acceptable biodegradation (the ability to safely degrade within the body), and are associated with easy and consistently reproducible (clinical grade) synthesis. In the experiments described herein, the DNA, siRNA, peptide or polypeptide-conjugated positively-charged highly branched polymeric dendrimer includes a peptide (e.g., PADRE or Influenza HA) that targets APCs and activates helper T cells in both humans and mice. The PADRE peptide has 2 main functions: escorting DNA to PAPCs as it binds to the MHC class-II present on the PAPCs and it stimulates T helper cells that promote the generation of cytotoxic T cells and the class switching required for antibody responses. This novel nanoconstruct has unique properties for gene and peptide delivery and vaccination. The experiments described herein also show that positively-charged highly branched polymeric dendrimers (PAMAM dendrimers) conjugated to PADRE delayed the growth of and reduced the size of established and highly aggressive B16/LU8 melanoma tumors in C57BL mice by 50% in a therapeutic setting and demonstrated 100% eradication of tumors in a B16/OVA preventative setting, induced robust immune responses against a gene product used for vaccination, demonstrated transfection efficiency in both mouse and human APCs by 2- or 3-fold, delivered a plasmid encoding GFP in vivo resulting in draining lymph nodes, and efficiently deliverd siRNA into human B cells, T cells, and murine macrophages.

The compositions and vaccines described herein are a tailored and ideal platform for vaccination, as they target MHC class II positive cells, all or nearly all of which are PAPCs. However, as importantly, MHC class II positive cells express very important co-inhibitory and co-stimulatory molecules (including but not limited to CD80, CD86, B7-H1, B7-H4, B7-DC, CD137, OX40, Foxp3 and their putative co-stimulatory receptor(s)) which suppress or promote T-cell activation. Targeted manipulation of the expression of molecules involved in these pathways can be used for i) the immunotherapy/vaccination for cancer, infectious diseases or other novel vaccine approaches such as vaccination for addiction or infertility or neutralizing a disease-inducing agent in a subject, as well as management of autoimmunity. Targeted delivery of vaccines to APCs as described herein offers a solution to the challenges associated with current vaccination strategies by resulting in much more robust immune responses, a reduction of suppressor/feedback mechanisms, and preventing toxicity by lowering the vaccine dose.

Accordingly, described herein is a vaccine including at least one charged highly branched polymeric dendrimer having conjugated thereto at least one T helper peptide and a nucleic acid encoding at least one antigen, wherein the at least one T helper peptide and the nucleic acid are conjugated to the exterior surface of the at least one charged highly branched polymeric dendrimer such that the at least one T helper peptide specifically binds to professional antigen presenting cells and the combination of the at least one T helper peptide, at least one charged highly branched polymeric dendrimer, and nucleic acid are able to induce an immune response against the at least one antigen. In the vaccine, the at least one dendrimer can be bound to Polyinosinic-polycytidylic acid. This embodiment can include a pharmaceutically acceptable carrier and/or a water-in-oil emulsion. In one embodiment, the at least one T helper peptide is a Pan-DR epitope (PADRE), e.g., two PADRE epitopes each having the amino acid sequence of SEQ ID NO:1. The at least one T helper peptide can also be influenza HA. The nucleic acid can be an expression vector and the at least one antigen can be a cancer antigen or an antigen from an infectious pathogen. The at least one charged highly branched polymeric dendrimer can be a PAMAM dendrimer.

Also described herein is a vaccine including at least one charged highly branched polymeric dendrimer having conjugated thereto at least one T helper peptide and at least one peptide or polypeptide antigen, wherein the at least one T helper peptide and the at least one peptide or polypeptide antigen are conjugated to the exterior surface of the at least one charged highly branched polymeric dendrimer such that the at least one T helper peptide specifically binds to professional antigen presenting cells and the combination of the at least one T helper peptide, at least one charged highly branched polymeric dendrimer and at least one peptide or polypeptide antigen are able to induce an immune response against the at least one peptide or polypeptide antigen. In one embodiment, the at least one charged highly branched polymeric dendrimer has further conjugated thereto a second peptide or polypeptide antigen that is different from the at least one peptide or polypeptide antigen. The vaccine can further include a second charged highly branched polymeric dendrimer having conjugated thereto at least one T helper peptide and a second peptide or polypeptide antigen that is different from the at least one peptide or polypeptide antigen, wherein the at least one T helper peptide and the second peptide or polypeptide antigen are conjugated to the exterior surface of the second charged highly branched polymeric dendrimer such that the at least one T helper peptide specifically binds to professional antigen presenting cells and the combination of the at least one T helper peptide, the second charged highly branched polymeric dendrimer and the second peptide or polypeptide antigen are able to induce an immune response against the second peptide or polypeptide antigen. The at least one charged highly branched polymeric dendrimer can be bound to Polyinosinic-polycytidylic acid. The vaccine can further include a pharmaceutically acceptable carrier and/or a water-in-oil emulsion. The at least one T helper peptide can be a Pan-DR epitope, e.g., two Pan-DR epitopes each having the amino acid sequence of SEQ ID NO:1. In another embodiment, the at least one T helper epitope is influenza HA. The at least one peptide or polypeptide antigen can be a cancer antigen or an antigen from an infectious pathogen. The at least one charged highly branched polymeric dendrimer can be a PAMAM dendrimer.

Further described herein is a method of delivering an antigen to a mammal and inducing production of monoclonal antibodies against the antigen in the mammal. The method includes the steps of: administering to the mammal a composition including at least one charged highly branched polymeric dendrimer having conjugated thereto at least one T helper peptide and at least one peptide or polypeptide antigen or a nucleic acid encoding the at least one antigen, wherein the at least one T helper peptide and the nucleic acid or at least one peptide or polyeptide antigen are conjugated to the exterior surface of the at least one charged highly branched polymeric dendrimer such that the at least one T helper peptide specifically binds to professional antigen presenting cells and the combination of the at least one T helper peptide, at least one charged highly branched polymeric dendrimer, and the nucleic acid or at least one peptide or polypeptide antigen are able to induce an immune response against the at least one peptide or polypeptide antigen, the composition in an amount effective to induce MHC class II mediated activation of helper T cells, wherein administering the composition to the mammal results in production of monoclonal antibodies against the at least one peptide or polypeptide antigen. In an embodiment wherein the mammal has cancer, the at least one peptide or polypeptide antigen is a cancer antigen, and the composition is a vaccine for the cancer. Typically, administration of the composition results in no local adverse reactions in the mammal. In another embodiment wherein the mammal has an infectious disease, the at least one peptide or polypeptide antigen is from an infectious pathogen, and the composition is a vaccine for the infectious pathogen, typically resulting in no local adverse reactions in the mammal. The at least one charged highly branched polymeric dendrimer can be bound to Polyinosinic-polycytidylic acid and/or can include a pharmaceutically acceptable carrier and/or water-in-oil emulsion.

In one embodiment of this method, the at least one T helper peptide is a PADRE epitope, e.g., two PADRE epitopes each having the amino acid sequence of SEQ ID NO:1. The at least one T helper peptide can also be influenza HA. The at least one charged highly branched polymeric dendrimer can be a PAMAM dendrimer. The at least one charged highly branched polymeric dendrimer can be further conjugated to a second peptide or polypeptide antigen that is different from the at least one peptide or polypeptide antigen. The composition can further include a second charged highly branched polymeric dendrimer having conjugated thereto at least one T helper peptide and a second peptide or polypeptide antigen that is different from the at least one peptide or polypeptide antigen, wherein the at least one T helper peptide and the second peptide or polypeptide antigen are conjugated to the exterior surface of the second charged highly branched polymeric dendrimer such that the at least one T helper peptide specifically binds to professional antigen presenting cells and the combination of the at least one T helper peptide, the second charged highly branched polymeric dendrimer and the second peptide or polypeptide antigen are able to induce an immune response against the second peptide or polypeptide antigen.

In one embodiment for producing and harvesting antibodies, the mammal can be a rodent or rabbit and the monoclonal antibodies are harvested from the mammal. In this embodiment, the monoclonal antibodies are prepared by the steps of: harvesting the antibodies from the mammal, titering the antibodies, removing the spleen from the mammal, and performing fusion with myeloma. The antibodies can be humanized.

Further described herein is a composition including at least one charged highly branched polymeric dendrimer having conjugated thereto at least one T helper peptide and at least one siRNA, wherein the at least one T helper peptide and the at least one siRNA are conjugated to the exterior surface of the charged highly branched polymeric dendrimer such that the at least one T helper peptide specifically binds to professional antigen presenting cells. The at least one charged highly branched polymeric dendrimer can be a PAMAM dendrimer, the at least one T helper peptide can be PADRE, and the siRNA can be directed against, for example, CTLA-4, Foxp3, CD28, IDO or Arginase 1.

Yet further described herein is a method of delivering siRNA into professional antigen presenting cells including the steps of: providing a composition including at least one charged highly branched polymeric dendrimer having conjugated thereto at least one T helper peptide and at least one siRNA, wherein the at least one T helper peptide and the at least one siRNA are conjugated to the exterior surface of the charged highly branched polymeric dendrimer such that the at least one T helper peptide specifically binds to professional antigen presenting cells; and administering the composition to a mammalian subject under conditions in which the at least one charged highly branched polymeric dendrimer having conjugated thereto at least one T helper peptide and at least one siRNA binds to a professional antigen presenting cell and the siRNA enters the professional antigen presenting cell. The charged highly branched polymeric dendrimer can be a PAMAM dendrimer, the at least one T helper peptide can be, for example, a PADRE, and the siRNA can be directed against, for example, CTLA-4, Foxp3, CD28, IDO or Arginase 1. In one embodiment, the siRNA prevents expression of CTLA-4, Foxp3, CD28, IDO or Arginase 1 in the professional antigen presenting cell.

Still further described herein is a method of inhibiting proliferation of MHC Class II tumor cells (e.g., lymphoma or a portion of a lymphoma) or inducing apoptosis of MHC Class II tumor cells in a mammal. This method includes the steps of: administering to the mammal a composition including at least one positively-charged highly branched polymeric dendrimer having conjugated thereto at least one T helper peptide and bound by a nucleic acid encoding a protein, wherein the at least one T helper peptide and the nucleic acid are conjugated and bound to the exterior surface of the at least one positively-charged highly branched polymeric dendrimer such that the at least one T helper peptide specifically binds to MHC Class II tumor cells and the combination of the at least one T helper peptide, at least one positively-charged highly branched polymeric dendrimer, and the nucleic acid or protein encoded by the nucleic acid inhibit proliferation of MHC Class II tumor cells or induce apoptosis of MHC Class II tumor cells. The positively-charged highly branched polymeric dendrimer can be, for example, a PAMAM dendrimer and the at least one T helper peptide can be, for example, a PADRE. However, any suitable positively-charged highly branched dendrimers and T helper peptides can be used.

A method for delivering a nucleic acid to a cell as described herein includes contacting the cell with a composition including at least one positively-charged highly branched polymeric dendrimer having conjugated thereto at least one T helper epitope and at least one nucleic acid encoding a peptide or protein, wherein the at least one T helper epitope and the nucleic acid are conjugated to the exterior surface of the at least one positively-charged highly branched polymeric dendrimer such that the at least one T helper epitope specifically binds to the cell, and the combination of the at least one T helper epitope, at least one positively-charged highly branched polymeric dendrimer, and the nucleic acid are internalized by the cell. In this method, the peptide or protein is typically expressed within the cell. Although any suitable positively-charged highly branched dendrimers and T helper peptides can be used, the positively-charged highly branched polymeric dendrimer can be a PAMAM dendrimer, for example, and the at least one T helper peptide can be a PADRE, for example.

A composition for delivering a nucleic acid to a cell as described herein includes at least one positively-charged highly branched polymeric dendrimer having conjugated thereto at least one T helper peptide and at least one nucleic acid encoding a peptide or protein, wherein the at least one T helper peptide and the nucleic acid are conjugated to the exterior surface of the at least one positively-charged highly branched polymeric dendrimer such that the at least one T helper peptide specifically binds to the cell, and the combination of the at least one T helper peptide, at least one positively-charged highly branched polymeric dendrimer, and the nucleic acid are internalized by the cell. The positively-charged highly branched polymeric dendrimer can be a PAMAM dendrimer, and the at least one T helper peptide can be a PADRE, for example. However, any suitable positively-charged highly branched dendrimers and T helper peptides can be used.

Unless otherwise defined, all technical terms used herein have the same meaning as commonly understood by one of ordinary skill in the art to which this invention belongs.

As used herein, a "nucleic acid" or a "nucleic acid molecule" means a chain of two or more nucleotides such as RNA (ribonucleic acid) and DNA (deoxyribonucleic acid), and chemically-modified nucleotides. A "purified" nucleic acid molecule is one that is substantially separated from other nucleic acid sequences in a cell or organism in which the nucleic acid naturally occurs (e.g., 30, 40, 50, 60, 70, 80, 90, 95, 96, 97, 98, 99, 100% free of contaminants). The terms include, e.g., a recombinant nucleic acid molecule incorporated into a vector, a plasmid, a virus, or a genome of a prokaryote or eukaryote. Examples of purified nucleic acids include cDNAs, fragments of genomic nucleic acids, nucleic acids produced polymerase chain reaction (PCR), nucleic acids formed by restriction enzyme treatment of genomic nucleic acids, recombinant nucleic acids, and chemically synthesized nucleic acid molecules. A "recombinant" nucleic acid molecule is one made by an artificial combination of two otherwise separated segments of sequence, e.g., by chemical synthesis or by the manipulation of isolated segments of nucleic acids by genetic engineering techniques.

When referring to an amino acid residue in a peptide, oligopeptide or protein, the terms "amino acid residue", "amino acid" and "residue" are used interchangably and, as used herein, mean an amino acid or amino acid mimetic joined covalently to at least one other amino acid or amino acid mimetic through an amide bond or amide bond mimetic.

As used herein, "protein" and "polypeptide" are used synonymously to mean any peptide-linked chain of amino acids, regardless of length or post-translational modification, e.g., glycosylation or phosphorylation.

When referring to a nucleic acid molecule, polypeptide, or infectious pathogen, the term "native" refers to a naturally-occurring (e.g., a wild-type (WT)) nucleic acid, polypeptide, or infectious pathogen.

As used herein, the term "antigen" or "immunogen" means a molecule that is specifically recognized and bound by an antibody.

When referring to an epitope (e.g., T helper epitope), by biological activity is meant the ability to bind an appropriate MHC molecule and, in the case of peptides useful for stimulating CTL responses, induce a T helper response and a CTL response against a target antigen or antigen mimetic.

The terms "specific binding" and "specifically binds" refer to that binding which occurs between such paired species as enzyme/substrate, receptor/agonist, antibody/antigen, etc., and which may be mediated by covalent or non-covalent interactions or a combination of covalent and non-covalent interactions. When the interaction of the two species produces a non-covalently bound complex, the binding which occurs is typically electrostatic, hydrogen-bonding, or the result of lipophilic interactions. Accordingly, "specific binding" occurs between a paired species where there is interaction between the two which produces a bound complex having the characteristics of an antibody/antigen or enzyme/substrate interaction. In particular, the specific binding is characterized by the binding of one member of a pair to a particular species and to no other species within the family of compounds to which the corresponding member of the binding member belongs.

As used herein, the terms "Pan-DR epitopes," "Pan-HLA-DR-binding epitope," "PADRE" and "PADRE peptides" mean a peptide of between about 4 and about 20 residues that is capable of binding at least about 7 of the 12 most common DR alleles (DR1, 2w2b, 2w2a, 3, 4w4, 4w14, 5, 7, 52a, 52b, 52c, and 53) with high affinity. "High affinity" is defined herein as binding with an $IC_{50}\%$ of less than 200 nm. For example, high affinity binding includes binding with an $IC_{50}\%$ of less than 3100 nM. For binding to Class II MHC, a binding affinity threshold of 1,000 nm is typical, and a binding affinity of less than 100 nm is generally considered high affinity binding. Construction and use of PADRE peptides is described in detail in U.S. Pat. No. 5,736,142 which is incorporated herein by reference.

A "T helper peptide" as used herein refers to a peptide recognized by the T cell receptor of T helper cells. For example, the PADRE peptides described herein are T helper peptides.

As used herein, the term "dendrimer" means a charged (e.g., positively-charged, negatively-charged), highly branched polymeric macromolecule with roughly spherical shape. An example of a positively-charged, highly branched polymeric dendrimer is a PAMAM dendrimer. By the terms "PAMAM dendrimer" and "poly-amidoamine dendrimer" is meant a type of dendrimer in which tertiary amines are located at branching points and connections between structural layers are made by amide functional groups.

By the terms "PAMAM dendrimer" and "poly-amidoamine dendrimer" is meant a type of dendrimer in which tertiary amines are located at branching points and connections between structural layers are made by amide functional groups. PAMAM dendrimers exhibit many positive charges on their surfaces.

By the term "derivatized dendrimer" is meant a dendrimer having one or more functional groups conjugated to its surface.

A "PADRE-derivatized dendrimer" or "PADRE-dendrimer" is a nanoconstruct in which one or more PADRE peptides are covalently attached to the functional groups on the surface of a charged (e.g., positively-charged) highly branched polymeric dendrimer (e.g., a PAMAM dendrimer).

By the term "conjugated" is meant when one molecule or agent is physically or chemically coupled or adhered to another molecule or agent. Examples of conjugation include covalent linkage and electrostatic complexation. The terms "complexed," "complexed with," and "conjugated" are used interchangeably herein.

As used herein, the phrase "sequence identity" means the percentage of identical subunits at corresponding positions in two sequences (e.g., nucleic acid sequences, amino acid sequences) when the two sequences are aligned to maximize subunit matching, i.e., taking into account gaps and insertions. Sequence identity can be measured using sequence analysis software (e.g., Sequence Analysis Software Package from Accelrys CGC, San Diego, Calif.).

The phrases "isolated" or biologically pure" refer to material which is substantially or essentially free from components which normally accompany it as found in its native state.

As used herein, the term "nanoparticle" means a microscopic particle whose size is measured in nanometers. For example, a nanoparticle is a PADRE-dendrimer conjugate or a particle combining several PADRE-dendrimer conjugates and nucleic acid or amino acid material with a total diameter in the range of approximately 2-500 nm.

The term "antibody" is meant to include polyclonal antibodies, monoclonal antibodies (mAbs), chimeric antibodies, humanized antibodies, anti-idiotypic (anti-Id) antibodies to antibodies that can be labeled in soluble or bound form, as well as fragments, regions or derivatives thereof, provided by any known technique, such as, but not limited to, enzymatic cleavage, peptide synthesis or recombinant techniques.

As used herein the term "adjuvant" means any material which modulates to enhance the humoral and/or cellular immune response.

As used herein, the terms "displayed" or "surface exposed" are considered to be synonyms, and refer to antigens or other molecules that are present (e.g., accessible to immune site recognition) at the external surface of a structure such as a nanoparticle (e.g., PADRE-dendrimer).

By the term "multivalent" is meant that more than one copy or type of antigen or molecule is displayed on a nanoparticle.

As used herein, "vaccine" includes all prophylactic and therapeutic vaccines. The vaccine compositions described herein are suitable for administration to subjects in a biologically compatible form in vivo. The expression "biologically compatible form suitable for administration in vivo" as used herein means a form of the substance to be administered in which any toxic effects are outweighed by the therapeutic effects. The substances may be administered to any animal, e.g., humans. In some embodiments, a vaccine as described herein is administered to a mammal, e.g., a rodent or rabbit, for producing monoclonal antibodies against a particular antigen.

By the phrase "immune response" is meant induction of antibody and/or immune cell-mediated responses specific against an antigen or antigens. The induction of an immune response depends on many factors, including the immunogenic constitution of the challenged organism, the chemical composition and configuration of the antigen, and the manner and period of administration of the antigen. An immune response has many facets, some of which are exhibited by the cells of the immune system (e.g., B-lymphocytes, T-lymphocytes, macrophages, and plasma cells). Immune system cells may participate in the immune response through interaction with an antigen or other cells of the immune system, the release of cytokines and reactivity to those cytokines. Immune responses are generally divided into two main categories—humoral and cell-mediated. The humoral component of the immune response includes production of antibodies specific for an antigen. The cell-mediated component includes the generation of delayed-type hypersensitivity and cytotoxic effector cells against the antigen.

By the phrases "therapeutically effective amount" and "effective dosage" is meant an amount sufficient to produce a therapeutically (e.g., clinically) desirable result; the exact nature of the result will vary depending on the nature of the disorder being treated. For example, where the disorder to be treated is cancer, the result can be elimination of cancerous cells including cancerous tumors. The compositions and vaccines described herein can be administered from one or more times per day to one or more times per week. The skilled artisan will appreciate that certain factors can influence the dosage and timing required to effectively treat a subject, including but not limited to the severity of the disease or disorder, previous treatments, the general health and/or age of the subject, and other diseases present. Moreover, treatment of a subject with a therapeutically effective amount of the compositions or vaccines of the invention can include a single treatment or a series of treatments.

As used herein, the term "treatment" is defined as the application or administration of a therapeutic agent described herein, or identified by a method described herein, to a patient, or application or administration of the therapeutic agent to an isolated tissue or cell line from a patient, who has a disease, a symptom of disease or a predisposition toward a disease, with the purpose to cure, heal, alleviate, relieve, alter, remedy, ameliorate, improve or affect the disease, the symptoms of disease, or the predisposition toward disease.

The terms "patient" "subject" and "individual" are used interchangeably herein, and mean a mammalian subject to be treated, with human patients being preferred. In some cases, the methods of the invention find use in experimental animals, in veterinary applications, and in the development of animal models for disease, including, but not limited to, rodents including mice, rats, and hamsters, as well as non-human primates.

Although vaccines, compositions, kits and methods similar or equivalent to those described herein can be used in the practice or testing of the present invention, suitable vaccines, compositions, kits and methods are described below. All publications, patent applications, and patents mentioned herein are incorporated by reference in their entirety. In the case of conflict, the present specification, including definitions, will control. The particular embodiments discussed below are illustrative only and not intended to be limiting.

BRIEF DESCRIPTION OF THE DRAWINGS

FIG. 1 illustrates that the PADRE-dendrimers described herein provide a platform in which any antigen of interest or nucleic acid encoding any antigen of interest can be incorporated. The PADRE-dendrimers described herein are activators of innate immunity that are designed to be grabbed by professional APCs.

FIG. 3 a series of photographs showing in vivo DNA delivery of PADRE-dendrimers. PADRE-dendrimer/GFP-plasmid complexes were injected into skin (5 µg total plasmid) and cornea (1 µg/cornea). Stereo fluorescent microscope images were taken on live anesthetized mice. The left image shows the GFP expression in skin and the image on the right shows GFP expression in the cornea.

FIG. 4 is a graph showing treatment of established tumors in mice. C57BL mice were immunized with plasmids encoding for either GFP (once) or OVA (twice) subcutaneously. The sera of three mice were collected and ELISA (left) or FLISA (right) were performed.

FIG. 8 is a series of flow cytometry dot plots showing the in vivo targeting of DCs in the lymph node. The left image depicts a schematic of a timeline for injection and lymph node removal and analysis and the right image shows a pair of flow cytometry dot plots upon analysis of data obtained from cells of the lymph node adjacent to PDD/GFP-plasmid or Dendrimer/GFP-plasmid injection site versus a naïve lymph node. These images show the efficacy of in vivo PADRE-denhdrimer targeting of mouse DCs and B cells in an injection site neighboring the lymph node. Lymph cells were stained with CD11c (DC marker), MHC class II and CD20 (B cell marker). The histograms in the right top show that Dendrimer/GFP-plasmid injection resulted in the expression of GFP in approximately 6% of DCs while the lower dot plot clearly shows that PDD/GFP-plasmid injection resulted in the expression of GFP in >70% of DCs.

FIG. 16 is a pair of photographs of multi-well plates upon in-cell Western assay using sera of immunized mice showing induction of antibody responses in mice upon one immunizations with PDD/plasmid-VgPCR that was further mounted upon a second immunization with PDD/plasmid-VgPCR. These results show that a single immunization with PDD/plasmid-VgPCR results in an antibody response which was enhanced upon a booster.

DETAILED DESCRIPTION

Figure 1:
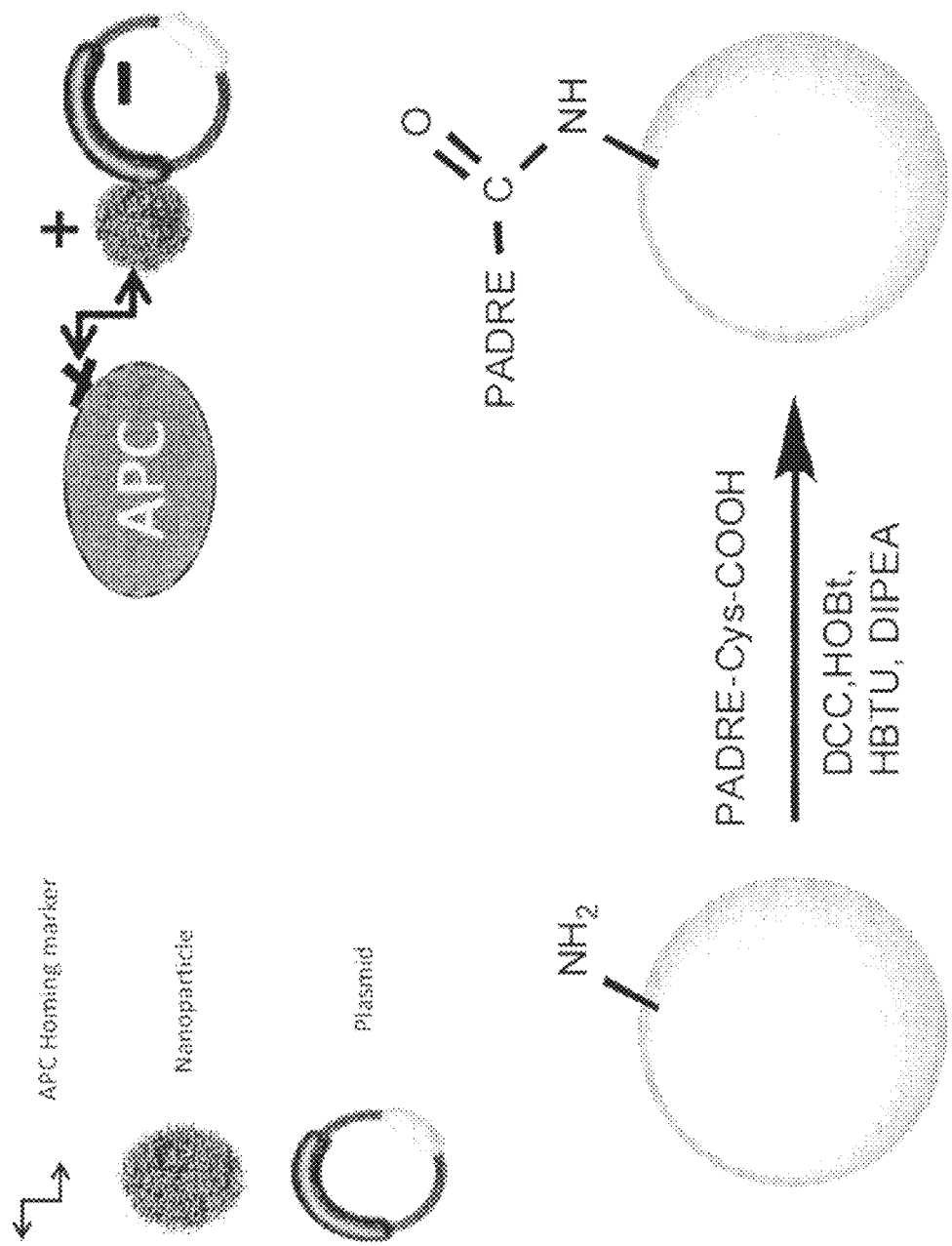
FIG. 1 is a pair of schematics showing the PADRE-dendrimer that may be mixed with plasmid or linked to a peptide or polypeptide antigen to target APCs.

Described herein are nanoparticle-based vaccines, compositions, kits and methods for effective delivery of one or more antigens in vivo for vaccination and antibody (e.g., monoclonal antibody) production, and for the effective delivery of peptides, proteins, siRNA, RNA or DNA to PAPCs or MHC class II positive cells (e.g. tumor cells). In a typical vaccine or composition, a charged (e.g., positively-charged), highly branched polymeric dendrimer is conjugated to an MHC targeting and immunogenic peptide such as a T helper peptide (e.g., an epitope such as the PADRE peptide or Influenza HA, etc.) and conjugated or bound to at least one molecule for inducing an immune response to a particular antigen in a subject. The molecule may be a protein or peptide of bacterial, fungal, protozoan, or viral origin, or a fragment derived from these antigens, a carbohydrate, or a carbohydrate mimetic peptide. The molecule may also include self-antigens for the treatment of autoimmune diseases. Additionally, the antigenic molecule(s) may also include one or more nucleic acids including those in a mammalian plasmid encoding for at least one antigen. For example, antigens may be one or more nucleic acids that result in expression of one or more immunogenic proteins and induction of a robust and specific immune response to the expressed protein(s) in a subject (e.g., mammal). As another example, antigens may also be immunogenic peptides or polypeptides that are processed and presented. A charged (e.g., positively-charged), highly branched polymeric dendrimer can be conjugated to two or more different antigens and similarly, can be conjugated to two or more nucleic acids that each encode a different antigen. A vaccine or other composition as described herein can include a plurality of charged (e.g., positively-charged), highly branched polymeric dendrimers that are conjugated to one type of antigen (e.g., five dendrimers conjugated to five copies of a particular antigen), or a plurality of charged (e.g., positively-charged), highly branched polymeric dendrimers conjugated to a plurality of different antigens (e.g., five dendrimers conjugated five different antigens). The dendrimer makes a complex (conjugation) with antigens (nucleic acids or proteins) based on the opposite charge of the dendrimer (positive) and that of antigen (negative) or the conjugation may be a covalent chemical linkage.

In one embodiment, a nanoparticle-based method to deliver antigens in vivo as described herein includes injection of a vaccine composed of a DNA plasmid encoding an antigen bound to, or an antigenic peptide or polypeptide conjugated to a charged (e.g., positively-charged), highly branched polymeric dendrimer (e.g., PADRE-derivatized dendrimer (PDD)) that is also conjugated to an MHC targeting and immunogenic peptide such as a T helper peptide (e.g., an epitope such as the PADRE peptide or Influenza HA, etc.). Negatively-charged plasmids bind naturally to the positively-charged PADRE-dendrimers, while peptide or polypeptide antigens can be chemically linked to the PADRE-dendrimers if they are not negatively-charged. In other embodiments, a dendrimer is negatively-charged for binding to positively-charged proteins and peptides. Surface-exposed antigen(s) or nucleic acid(s) encoding an antigen(s) may be conjugated to the dendrimers by any suitable means known in the art. Conjugation methods include chemical complexation, which may be either ionic or nonionic in nature, electrostatic binding, or covalent binding. A dendrimer conjugated to a T helper epitope as described herein can be multivalent; it can present more than one copy or type of antigen or nucleic acid on its surface. Presentation of multivalent or aggregated antigens (or nucleic acids encoding antigens) may improve the immune response of a subject. The one or more copies or types of antigens or nucleic acids can be attached to the dendrimer via two or more separate linkers or spacers, or via a common linker or spacer. The compositions, kits and vaccines described herein have both prophylactic and treatment applications, i.e., can be used as a prophylactic to prevent onset of a disease or condition in a subject, as well as to treat a subject having a disease or condition. A vaccine as described herein can be used to mount an immune response against any infectious pathogen or cancer.

The therapeutic agents described herein can be used to target mononuclear cells, in particular B cells, and can be used to treat concurrent B-cell chronic lymphocytic leukemia, and Multiple myeloma. A combination of nanoparticle as described herein (e.g., PADRE-derivatized dendrimer) and therapeutic agent (e.g., drug) may be used in several forms, e.g., a mixture of the nanoparticle with the therapeutic agent, electrostaticlly bound to form a complex, chemical conjugation of the therapeutic agent to the nanoparticle, etc. Examples of therapeutic agents includes but are not limited to toxins, iRNA, siRNA, microRNA, plasmid (e.g., encoding tumor suppressor genes, suicide genes (e.g., TK) or any genes the block or alter tumor proliferation and/or survival), Taxol® (paclitaxel) (Bristol-Myers Squibb), antibodies, melphalan, prednisone, thalidomide (MPT), Velcade® (bortezomib) (Millenium Pharmaceuticals), lenalidomide, and dexamethasone or any combination of such agents.

Similarly, the compositions and methods described herein may be used for the therapy of autoimmune disorders, where the therapeutic agent reaches (be delivered to) immune cells including monocytes, DCs, T cells or B cells. The compositions described herein may be used with adjuvants such as (but not limited to) Poly I:C which is negatively charged and makes a complex with the nanoparticle platform as described herein.

The below described preferred embodiments illustrate adaptations of these compositions, vaccines, kits and methods. Nonetheless, from the description of these embodiments, other aspects of the invention can be made and/or practiced based on the description provided below.

Biological Methods

Methods involving conventional molecular biology techniques are described herein. Such techniques are generally known in the art and are described in detail in methodology treatises such as Molecular Cloning: A Laboratory Manual, 3rd ed., vol. 1-3, ed. Sambrook et al., Cold Spring Harbor Laboratory Press, Cold Spring Harbor, N.Y., 2001; and Current Protocols in Molecular Biology, ed. Ausubel et al., Greene Publishing and Wiley-Interscience, New York, 1992 (with periodic updates). Immunology techniques are generally known in the art and are described in detail in methodology treatises such as Advances in Immunology, volume 93, ed. Frederick W. Alt, Academic Press, Burlington, Mass., 2007; Making and Using Antibodies: A Practical Handbook, eds. Gary C. Howard and Matthew R. Kaser, CRC Press, Boca Raton, Fla., 2006; Medical Immunology, $6^{th}$ ed., edited by Gabriel Virella, Informa Healthcare Press, London, England, 2007; and Harlow and Lane ANTIBODIES: A Laboratory Manual, Cold Spring Harbor Laboratory Press, Cold Spring Harbor, N.Y., 1988. Conventional methods of gene transfer and gene therapy may also be adapted for use in the present invention. See, e.g., Gene Therapy: Principles and Applications, ed. T. Blackenstein, Springer Verlag, 1999; and Gene Therapy Protocols (Methods in Molecular Medicine), ed. P. D. Robbins, Humana Press, 1997. Methods of vaccine production and administering vaccines are also generally known in the art and are described in detail, for example, in Vaccine Protocols (Methods in Molecular Medicine) by Andrew Robinson, Martin P. Cranage, and Michael J. Hudson, 2nd ed., Humana Press, Totowa, N.J., 2003;

Vaccine Adjuvants and Delivery Systems, by Manmohan Singh, 1st ed., Wiley-Interscience, Hoboken, N.J., 2007; Arvin A. M. and Greenberg H. B., Virology 344:240-249, 2006; and R. Morenweiser, Gene Therapy suppl.1:S103-S110, 2005. Construction and use of vaccines as well as PAMAM dendrimers is also described, for example, in Arashkia et al., Virus Genes 40 (1): 44-52, 2010; Velders et al., J Immunol. 166:5366-5373, 2001; and S. Chauhan, N. K. Jain, P. V. Diwan. (2009) Pre-clinical and behavioural toxicity profile of PAMAM dendrimers in mice. Proceedings of the Royal Society A: Mathematical, Physical and Engineering Sciences (Online publication date: Dec. 3, 2009).

Synthesis of Dendrimers Conjugated to Nucleic Acids, Peptides or Polypeptides

Dendrimers act as scaffolds to condense DNA, and a fully positively-charged dendrimer is preferable for developing strong electrostatic interactions with a negatively-charged DNA or RNA. A resulting dendrimer/T helper epitope/DNA complex, for example, has a net charge depending on the adjustable N/P ratio (amine to phosphate or charge ratio). Described herein are dendrimers having conjugated thereto T helper peptides (e.g., an epitope such as the PADRE peptide or Influenza HA) and an antigen, a nucleic acid encoding an antigen, or an siRNA, wherein the at least one T helper peptide and the antigen, nucleic acid or siRNA are conjugated to the exterior surface of the dendrimer such that the at least one T helper peptide specifically binds to PAPCs. In one embodiment, dendrimers are conjugated to at least one PADRE peptide (e.g., 2, 3, 4, 5, etc.) and a peptide or polypeptide antigen. In this embodiment, a dendrimer is typically conjugated to or bound to (e.g., via an electrostatic binding) to a plurality of the peptide or polypeptide antigen. Conjugating or binding several antigens (e.g., a plurality of the same antigen) may be particularly useful when the antigen is a small antigen (especially small peptides or carbohydrates), as small antigens generally fail to elicit an effective immune response due to hapten-related size issues. Including multiple copies of an antigen into the dendrimer/T helper peptide/nucleic acid conjugates described herein can thus enhance the immunogenicity of the antigen. In another embodiment, dendrimers are conjugated to PADRE peptides and bound to a nucleic acid encoding an antigen. In yet another embodiment, dendrimers are conjugated to PADRE peptides and bound to an siRNA directed against a gene of interest. In these embodiments, the dendrimers can be prepared and conjugated to a T helper peptide (e.g., an epitope such as the PADRE peptide or Influenza HA) and bound to nucleic acid (e.g., DNA, siRNA) or peptide or polypeptide using any suitable method. Methods of producing and using dendrimers are well known in the art and are described, for example, in Zhang J-T et. al. Macromol. Biosci. 2004, 4, 575-578, and U.S. Pat. Nos. 4,216,171 and 5,795,582, both incorporated herein by reference. See also: D. A. Tomalia, A. M. Naylor, and W. A. Goddard III, "Starburst Dendrimers: Molecular-Level Control of Size, Shape, Surface Chemistry, Topology, and Flexibility from Atoms to Macroscopic Matter", Angew. Chem. Int. Ed. Engl. 29 (1990), 138-175. In the experiments described herein, PAMAM dendrimers were used. However, any suitable positively charged, highly branched polymeric dendrimer can be used. Examples of additional positively charged, highly branched polymeric dendrimers include poly(propylene imine) (PPI) dendrimers or, more generally, any other dendrimers with primary amine groups on their surfaces.

The PADRE-dendrimers (PADRE-derivatized dendrimers) described herein can be prepared by any suitable method. Methods of making and using PADRE are known in the art. See, for example, U.S. Pat. No. 5,736,142. To produce the PADRE peptides described in U.S. Pat. No. 5,736,142, a strategy initially described by Jardetzky et al. (EMBO J. 9:1797-1083, 1990) was used, in which anchor residues that contain side chains critical for the binding to MHC are inserted into a poly-alanine peptide of 13 residues. PADRE peptides can be prepared according to the methods described in U.S. Pat. No. 5,736,142, for example, or they can be purchased (e.g., from Anaspec, Inc., Fremont, Calif.). Because of their relatively short size, the PADRE peptides can be synthesized in solution or on a solid support in accordance with conventional techniques. Various automatic synthesizers are commercially available and can be used in accordance with known protocols. Alternatively, recombinant DNA technology may be employed wherein a nucleotide sequence which encodes a T helper epitope is inserted into an expression vector, transformed or transfected into an appropriate host cell and cultivated under conditions suitable for expression. These procedures are generally known in the art, as described generally in Sambrook et al., (supra), which is incorporated herein by reference. PADRE peptides as described herein may include modifications to the N- and C-terminal residues. As will be well understood by the artisan, the N- and C-termini may be modified to alter physical or chemical properties of the peptide, such as, for example, to affect binding, stability, bioavailability, ease of linking, and the like. The PADRE peptides described herein may be modified in any number of ways to provide desired attributes, e.g., improved pharmacological characteristics, while retaining substantially all of the biological activity of the unmodified peptide.

In the experiments described herein, the PADRE-dendrimer conjugate was made by simple amide coupling between the —COOH terminus of the PADRE peptide and one of the dendrimer amine groups. The PADRE peptide (Ac-D-Ala-Lys-Cha-Val-Ala-Ala-Trp-Thr-Leu-Lys-Ala-Ala-Ala-D-Ala-Ahx-Cys-OH) (SEQ ID NO:1, Ac=acetylated; D-Ala=D-alanine; Cha=cyclohexylalanine; Ahx=aminohexanoic acid) was purchased from Anaspec, Inc., (Fremont, Calif.) in its acetylated form in order to protect the amine terminus and prevent its reaction. The purchased peptide had a minimum purity of 95%. The amide coupling reaction was carried out under standard conditions (see FIG. 1, bottom schematic) in DMF solution. In order to control the number of PADRE epitopes attached to the surface of each dendrimer, a 2:1 peptide/dendrimer challenge ratio was used in the reaction, seeking attachment of just a few peptides per dendrimer in order to keep most of the amine groups free to develop large positive charges on the dendrimer. In a typical embodiment, a plurality of PADRE-dendrimer conjugates as described herein will be a distribution of dendrimers containing 0, 1, 2, 3, etc., PADREs (or other peptide) attached thereto. Relative populations are expected to follow the Poisson distribution. The PADRE, aKXVAAWTLKAAa (SEQ ID NO:2) binds with high or intermediate affinity ($IC_{50}$<1,000 nM) to 15 out of 16 of the most prevalent HLA-DR molecules ((Kawashima et al., Human Immunology 59:1-14 (1998); Alexander et al., Immunity 1:751-761 (1994)). However, other peptides which also can bind MHC class II and activate CD4 T helper cells in most humans may also be used to tag the dendrimer.

Examples of peptides include but are not limited to: tetanus toxoid (TT) peptide 830-843; the "universal" epitope described in Panina-Bordignon et al., (Eur. J. Immunology 19:2237-2242 (1989)); and the following peptides that react with MHC class II of most human HLA, and many of mice: aKFVAAWTLKAAa (SEQ ID NO:3), aKYVAAWTLKAAa (SEQ ID NO:4), aKFVAAYTLKAAa (SEQ ID NO:5), aKXVAAYTLKAAa (SEQ ID NO:6), aKYVAAYTLKAAa (SEQ ID NO:7), aKFVAAHTLKAAa (SEQ ID NO:8), aKXVAAHTLKAAa (SEQ ID NO:9), aKYVAAHTLKAAa (SEQ ID NO:10), aKFVAANTLKAAa (SEQ ID NO:11), aKXVAANTLKAAa (SEQ ID NO:12), aKYVAANTLKAAa (SEQ ID NO:13), AKXVAAWTLKAAA (SEQ ID NO:2), AKFVAAWTLKAAA (SEQ ID NO:14), AKYVAAWTLKAAA (SEQ ID NO:15), AKFVAAYTLKAAA (SEQ ID NO:16), AKXVAAYTLKAAA (SEQ ID NO:17), AKYVAAYTLKAAA (SEQ ID NO:18), AKFVAAHTLKAAA (SEQ ID NO:19), AKXVAAHTLKAAA (SEQ ID NO:20), AKYVAAHTLKAAA (SEQ ID NO:21), AKFVAANTLKAAA (SEQ ID NO:22), AKXVAANTLKAAA (SEQ ID NO:23), and AKYVAANTLKAAA (SEQ ID NO:24) (a=D-alanine, X=cyclohexylalanine). Another example of an epitope that may be used is the HA peptide sequence SFERFEIFPKE (SEQ ID NO:25) (from the provirus PR8 virus HA) that binds to mouse Balb/c MHC classII IaD.

The product was purified by dialysis against pure water for at least 24 h and then dried under vacuum. The collected product, a clear oil, was characterized by $^1$H NMR, UV-Vis and MALDI-TOF mass spectroscopy. The NMR spectra of the PADRE-dendrimer conjugate shows large peaks corresponding to the dendrimer protons and a small set of peaks for the peptide protons. The MALDI-TOF mass spectrum of the PADRE-dendrimer conjugate shows a peak at a m/z ratio ca. 3,000 units higher than the peak observed for the dendrimer on its own. The excess mass corresponds to approximately 2 peptide epitopes. The UV-Vis spectrum of the conjugate shows a clear absorption in the wavelength range where tryptophan absorbs.

Complexation of plasmid DNA with the PADRE-dendrimer conjugate was done by mixing the two components in aqueous solution buffered at physiological pH with PBS. Typical N/P (amine to phosphate) ratios are 10:1. Gel electrophoresis is used to show complete complexation of the DNA. At physiological pH values, the amino groups (—NH$_2$) are protonated, affording a high positive charge to the dendrimers and making them particularly well-suited for the delivery of negatively-charged DNA or RNA into cells. In aqueous solution, the positively-charged dendrimers and the negatively-charged nucleic acids give rise to condensates or nanoparticles which can penetrate and traverse biological membranes with relative ease.

Dendrimers that are conjugated to T helper epitopes other than PADRE are typically prepared by a method similar to that described above for PADRE-derivatized dendrimers. For example, the acid terminus of the peptide can be covalently attached to one of the amine groups on the dendrimer surface by a number of well-known synthetic methods, such as amidation using carbodiimides as activating reagents As another example, attachment of these peptides to amino-terminated dendrimers is performed using two synthetic routes. The amino terminus of the peptide epitope is protected by acetylation. The first route uses the carboxylic acid of the terminal cysteine residue to achieve attachment via standard amidation chemistry. The second route takes advantage of the cysteine's thiol (if present on the peptide, otherwise may be added) to react it with the alkene groups added to the dendrimer surface by previous treatment with maleimide. Both routes allow the functionalization of dendrimers with epitopes. Up to several peptide epitopes (e.g., 2, 3, 4, 5, 6, etc.) per dendrimer will enhance the targeting property of the DNA delivery agents, improving their properties for vaccination purposes. However, it is important to leave a large number of unreacted amine groups so that the dendrimer will acquire a large positive charge via protonation at physiological pH values. Dendrimers as described herein can be conjugated to any T helper epitope. An example of an additional T helper epitope is Influenza HA.

Generally, generation-5 (G5) dendrimers are used in the compositions, kits and methods described herein. However, other generation dendrimers (see Table 1) can be used.

TABLE 1

PAMAM Dendrimers

| Generation | Molecular Weight | Diameter (nm) | Surface Groups |
|---|---|---|---|
| 0 | 517 | 1.5 | 4 |
| 1 | 1,430 | 2.2 | 8 |
| 2 | 3,256 | 2.9 | 16 |
| 3 | 6,909 | 3.6 | 32 |
| 4 | 14,215 | 4.5 | 64 |
| 5 | 28,826 | 5.4 | 128 |
| 6 | 58,0548 | 6.7 | 256 |

Charged Polymeric Carrier Vaccines and Compositions

A vaccine as described herein includes at least one charged (e.g., positively-charged) polymeric carrier such as a dendrimer having conjugated or bound thereto an MHC targeting and immunogenic peptide such as a T helper peptide (e.g., an epitope such as the PADRE peptide or Influenza HA) and at least one peptide or polypeptide antigen or at least one nucleic acid encoding the at least one antigen such that the at least one MHC targeting and immunogenic peptide and the at least one nucleic acid or at least one peptide or polypeptide antigen are conjugated to the exterior surface of the charged (e.g., positively-charged) polymeric carrier (e.g., dendrimer) and the MHC targeting and immunogenic peptide (e.g., T helper epitope) specifically binds to PAPCs. The combination of the at least one T helper peptide, at least one dendrimer and at least one peptide or polypeptide antigen or at least one nucleic acid encoding the at least one antigen are able to induce an immune response against the at least one antigen including induction of MHC class II mediated activation of helper T cells. A vaccine may further include a water-in-oil emulsion. Administering the vaccine to the mammal results in production of monoclonal antibodies against the antigen. Antigen or antigens as described herein that are displayed on or within the dendrimers induce an immune response against onset of disease caused by a variety of pathogenic conditions. In one embodiment, the antigen may be derived from, but are not limited to, pathogenic bacterial, fungal, or viral organisms, *Streptococcus* species, *Candida* species, *Brucella* species, *Salmonella* species, *Shigella* species, *Pseudomonas* species, *Bordetella* species, *Clostridium* species, Norwalk virus, *Bacillus anthracis, Mycobacterium tuberculosis*, human immunodeficiency virus (HIV), *Chlamydia* species, human Papillomaviruses, Influenza virus, Paramyxovirus species, Herpes virus, Cytomegalovirus, Varicella-Zoster virus, Epstein-Barr virus, Hepatitis viruses, *Plasmodium* species, *Trichomonas* species, sexually transmitted disease agents, viral encephalitis agents, protozoan disease agents, fungal disease agents, bacterial disease agents, cancer cells, or mixtures thereof.

The at least one dendrimer can be further conjugated to Polyinosinic-polycytidylic acid (Poly(I:C)), and the vaccine or composition can further include a pharmaceutically acceptable carrier. In one embodiment, the at least one T helper epitope is a Pan-DR epitope, e.g., two Pan-DR epitopes each having the amino acid sequence of SEQ ID NO:1. In another embodiment, the T helper epitope is influenza HA. The T helper epitope, however, can be any epitope that activates or contributes to activation of CD4+ T helper cells. T helper epitope activation of CD4+ T helper cells is required for the expansion and stimulation of CD8 T cells as well as for antibody production by B cells, both of which are essential for induction of protective immune responses against infectious agents or cancer. In an embodiment in which the dendrimer is conjugated to a nucleic acid encoding an antigen, the nucleic acid is generally an expression vector. The expression vector typically includes a eukaryotic promoter operably linked to a gene encoding the antigen, a cloning site, a polyadenylation sequence, a selectable marker and a bacterial origin of replication. Generally, the antigen is typically a cancer antigen or an antigen from an infectious pathogen. The at least one dendrimer is generally a G5 dendrimer. Similarly, in embodiments in which the dendrimer is conjugated to a peptide or polypeptide antigen, the antigen is generally a cancer antigen or an antigen from an infectious pathogen, and the at least one dendrimer is a G5 dendrimer. In some embodiments, an adjuvant may be incorporated in the vaccine or composition.

Dendrimers are effective vehicles to escort DNA (and other nucleic acids including DNA, RNA, siRNA, microRNA, RNAi, etc.) into cells. However, as a vaccine delivery platform, dendrimers have traditionally been a failure for several reasons. First, dendrimers lack adjuvant activity; they lack effective stimulation of innate immunity, and they do not generate a "danger signal". Also, dendrimers provide poor targeting of APCs and in general, they provide poor stimulation of adaptive immunity. A robust adjuvanted vaccine delivery system that specifically targets PAPCs, that induces a "danger signal," that recruits professional mononuclear cells to injection sites, and that is safe is highly desired, particularly when dealing with poor antigens with low immunogenicity or "self" antigens or those with high homology with "self" antigens against which the immune system has developed tolerance. Poor antigens or those with low immunogenicity result in no or low levels of specific immune responses, antibody responses or cell-mediated immune responses. The vaccine platform described herein is a biodegradable nanoparticle complexed with (conjugated to) DNA or a peptide or polypeptide antigen. The platform targets PAPCs via its MHC class II ligand, binds and penetrates the cell membrane by its highly positively-charged outer membrane, is safe and easy to scale up for high-volume production, and acts as a strong adjuvant due to the nature of modifications on the molecule. In a typical embodiment, the at least one dendrimer is a G5 PAMAM dendrimer that is a highly branched polymeric macromolecule and an ideal excipient for its enhanced solubility. G5 is, in particular, ideal for the delivery of DNA into cells. A typical vaccine as described herein includes a water-in-oil emulsion that induces a transient danger signal resulting in the recruitment of mononuclear cells to the injection site. These cells, upon picking up the DNA, will travel to regional lymph nodes and present antigen. Inclusion of a universal T helper agonist, e.g., PADRE, which binds to the flank of the MHC class II molecules, results in an opsinizing dendrimer complex for PAPCs as well as helper T cells. This alteration changes an inert and weak dendrimer to a robust immune enhancer for the expressed antigen of interest. Also including a hydrophobic career, i.e., an oil emulsion (e.g., Montanide ISA 720), that has both adjuvant activity as well as a depot effect, results in a slow release of antigen. Inclusion of poly(I:C) further enhances induction of an immune response against an antigen of interest. Since poly(I:C) has a negative net charge, it conveniently binds to dendrimer, and it is an adjuvant that enhances the robustness of an immune response. These features act as strong "danger signals" and recruit further mononuclear cells (including APCs) to the injection site. Collectively, these features stimulate innate immunity and result in enhanced expression of a proinflammatory cytokine milieu needed for inducing effective immune responses.

In one embodiment of a vaccine, the T helper peptide is a PADRE epitope and the dendrimer is PADRE-derivatized. PADRE is an artificially designed peptide that binds to the majority of MHC Class II, and conjugating PADRE peptides to dendrimers (e.g., a PADRE-derivatized dendrimer) makes the resultant complex or conjugate a ligand for PAPCs that express high levels of MHC class II. This complex thus becomes a universal targeted vaccine delivery system with high affinity for cells expressing MHC class II or PAPCs. PADRE also activates T helper cells and results in a milieu of proinflammatory cytokines, and recruits other immune cells to the injection site. Combined with a dendrimer, PADRE further enhances the uptake of antigen by inducing a "danger signal." A PADRE-derivatized dendrimer provides several advantages over currently known vaccines. First, a G5 dendrimer is a highly charged biodegradable molecule that will bind and enter a cell membrane very efficiently resulting in robust expression of the protein. Second, PADRE is a universal T-helper epitope that binds to many murine and human MHC class II molecules. It is a synthetic, non-natural T helper epitope [AKchxAVAAWTL-KAAA (SEQ ID NO:26) (chxA=cyclohexylalanine)]. When fused to the surface of the dendrimer, PADRE will bind and activate primarily cells that have MHC class II including all PAPCs. Several PADRE epitopes (e.g., 2, 3, 4, 5, etc.) can be attached to each dendrimer. The attachment is done with suitable spacers to preserve the binding properties of the peptide that give rise to its immunogenic properties. A linker or spacer molecule may be used in conjugating antigen or other molecules to the dendrimer conjugates described herein. Spacers may be any combination of amino acids including AAA, KK, GS, GSGGGGS (SEQ ID NO:27), RS, or AAY. As used herein, the terms "linker" or "spacer" mean the chemical groups that are interposed between the dendrimer and the surface exposed molecule(s) such as the MHC class II ligand, CD4+ T helper epitope, polypeptide, or therapeutic agent that is conjugated or bound to the dendrimer (e.g., PADRE-dendrimer) and the surface exposed molecule(s). Preferably, linkers are conjugated to the surface molecule at one end and at their other end to the nanoparticle (e.g., PADRE-dendrimer). Linking may be performed with either homo- or heterobifunctional agents, i.e., SPDP, DSS, SIAB. Methods for linking are disclosed in PCT/DK00/00531 (WO 01/22995) to deJongh, et al., which is hereby incorporated by reference in its entirety.

Third, in embodiments in which the vaccine also includes a water-in-oil emulsion, the water-in-oil emulsion induces a transient "danger signal" resulting in the recruitment of mononuclear cells to the injection site. These cells, upon picking up the DNA, will travel to regional lymph nodes and present antigen. In addition, to further enhance induction of an immune response, a synthetic double-stranded RNA (dsRNA), poly(I:C), can be bound to the dendrimer (e.g., a PADRE-dendrimer). Poly(I:C) is a Toll-like receptor 3 (TLR-3) agonist that has a negative net charge and thus conveniently binds to dendrimer. Poly(I:C) is an adjuvant and due to its negative net charge, will bind to the dendrimer and enhance robustness of the immune response. Binding Poly(I:C) to dendrimers is of particular use for the production of monoclonal antibodies (discussed below) because it reduces the frequency of and intervals between injections.

Nucleic acid molecules encoding an antigen as described herein may be in the form of RNA (e.g., mRNA, microRNA, siRNA, shRNA or synthetic chemically modified RNA) or in the form of DNA (e.g., cDNA, genomic DNA, and synthetic DNA). The DNA may be double-stranded or single-stranded, and if single-stranded, may be the coding (sense) strand or non-coding (anti-sense) strand. In one embodiment, a nucleic acid can be an RNA molecule isolated or amplified from immortalized or primary tumor cell lines.

As described above, in one embodiment, a vaccine for inducing an immune response includes at least one dendrimer having conjugated thereto at least one T helper epitope and a nucleic acid encoding an antigen, wherein the resultant complex induces an immune response against the antigen. These compositions and methods are far safer, simpler and rapid compared to other genetic immunization methods that require the use of viral vectors or in vivo electroporation, for example. The use of DNA for the induction of humoral or cellular immune responses has several advantages. First, use of DNA provides a full spectrum of naïve (naturally) processed epitopes. Also, dendrimers conjugated to a T helper epitope and a nucleic acid encoding an antigen provide a universal vaccine delivery targeted to APCs of >95% of all human MHCs (AKA, HLA) and eliminate the need for the purification of proteins that are challenging to purify. Such proteins can be part of a multi-protein complex, can be membrane proteins, and can be incorrectly folded and insoluble. The dendrimer conjugates described herein do not require glycoslyation or post-translational modifications of proteins, they tag interference with protein structure or folding, and offer dramatic cost and time savings. The fact that PADRE-dendrimer targets and delivers nucleic acids to PBMC from mice, Baboons and humans makes this platform an ideal candidate for rapid translational research from mice to non-human primates, and humans.

Also as described above, in another embodiment, a vaccine for inducing an immune response includes a water-in-oil emulsion and at least one dendrimer having conjugated thereto at least one T helper peptide (e.g., an epitope such as the PADRE peptide or Influenza HA) and a peptide or polypeptide antigen, wherein the at least one T helper epitope and the peptide or polypeptide antigen are conjugated to the exterior surface of the dendrimer and are able to induce an immune response against the peptide or polypeptide antigen. Peptides or polypeptides that have weak immunogenicity induce robust immune responses when conjugated to (complexed-with) T helper epitope/dendrimer complexes as described herein. Polypeptides and peptides with a negative net charge may complex with, for example, PADRE-dendrimer with no need for covalent conjugation. A water-in-oil emulsion of, for example, a PADRE-dendrimer results in further adjuvant activity and a depot effect.

As mentioned above, the compositions and vaccines described herein have both prophylactic and treatment applications; they can be used as a prophylactic to prevent onset of a disease or condition in a subject, as well as to treat a subject having a disease or condition. A vaccine as described herein can be used to mount an immune response against any infectious pathogen or cancer. Examples of infectious pathogens include viruses such as, but not limited to, influenza, HIV, dengue virus, rotavirus, HPV, HBV, HCV, CMV, HSV, HZV, and EBV, pathogenic agents including the causative agents of Malaria, *Plasmodium*(p) *falciparum, P. malariae, P. ovale, P. vivax* and *P. knowlesi*; the casatve agent of *Leishmania* (L), *L. major, L. tropica, L. aethiopica, L. mexicana, L. donovani, L. infantum syn. L. chagas*; pathogenic bacteria including *Bacillus anthracis, Bordetella pertussis, Streptococcus pneumonia*, and *meningococcus*. In the experiments described herein, PADRE-dendrimers eradicated established melanoma tumors in mice. However, the dendrimers conjugated to a T helper epitope and an antigen or a nucleic acid encoding an antigen as described herein can be used to mount a specific immune response against any cancer. Examples of additional cancers include HPV-induced cervical cancers (e.g., E7/E7 tumor associated antigens (TAA) or plasmids encoding for these antigens can be complexed with the T helper epitope/dendrimers (e.g. PADRE-dendrimer) described herein), human melanoma (e.g., TRP-1, TRP-2, gp-100, MAGE-1, MAGE-3 and/or p53 may be used as TAA and complexed with the T helper epitope/dendrimers (e.g. PADRE-dendrimer) described herein), and prostate cancer (e.g., TSA may be used as TAA and complexed with the T helper epitope/dendrimers (e.g. PADRE-dendrimer) described herein). Similarly for lung tumors, breast tumors, and leukemia, any suitable TAA can be used, and many have been described. Many such TAA are common between various cancers (e.g., CEA, MUC-1, Her2, CD20). A cocktail of TAA or plasmids encoding for such antigens may be used to make a universal, multiple-use cancer vaccine as described herein. In one example of a vaccine as described herein, a CD4 epitope/dendrimer (e.g., PADRE-dendrimer), may be complexed with more than one antigen or with more than one plasmid encoding the antigen. Alternatively, multiple vaccines each complexed with one antigen or with one plasmid encoding for one antigen may be mixed and used as one vaccine for various pathogens or various cancers.

Methods of Delivering an Antigen to a Mammal and Inducing an Immune Response

Described herein are methods of delivering an antigen to a mammal (e.g., human) and inducing production of monoclonal antibodies against the antigen for inducing a immune response in the mammal. A typical method includes the steps of: administering to the mammal a composition including at least one charged (e.g., positively-charged) polymeric carrier (e.g., a dendrimer) having conjugated thereto an MHC targeting and immunogenic peptide (e.g., a T helper peptide such as the PADRE peptide or Influenza HA, etc.) and at least one peptide or polypeptide antigen or at least one nucleic acid encoding the at least one antigen wherein the at least one T helper peptide and the at least one nucleic acid or at least one peptide or polyeptide antigen are conjugated to the exterior surface of the at least one charged (e.g., positively-charged) polymeric carrier (e.g., dendrimer) such that the at least one MHC targeting and immunogenic peptide (e.g., T helper epitope) specifically binds to PAPCs and the combination of the at least one MHC targeting and immunogenic peptide (e.g., T helper epitope), at least one charged (e.g., positively-charged) polymeric carrier (e.g., dendrimer), and the at least one nucleic acid or least one peptide or polypeptide antigen are able to induce an immune response against the antigen. In the method, the composition is administered in an amount effective to induce MHC class II mediated activation of helper T cells, resulting in production of monoclonal antibodies and an immune response against the antigen in the mammal. A composition can further include a water-in-oil emulsion. The at least one dendrimer is typically further conjugated to poly(I:C), and the composition typically further includes a pharmaceutically acceptable carrier. The at least one T helper epitope can be a Pan-DR epitope, e.g., two Pan-DR epitopes each having the amino acid sequence of SEQ ID NO:1. Alternatively, the at least one T helper epitope can be other than a Pan-DR epitope (PADRE epitope), e.g., influenza HA. Generally, the at least one dendrimer is a G5 dendrimer.

In one embodiment, the mammal has cancer, the antigen is a cancer antigen, and the composition is a vaccine for the cancer. In another embodiment, the mammal has an infectious disease, the antigen is an antigen from an infectious pathogen, and the composition is a vaccine for the infectious pathogen. In such embodiments, administration of the composition generally results in no local adverse reactions in the mammal. Such methods are generally performed by formulating the composition (e.g., vaccine) outside of the mammal and administering the composition to the mammal in an amount sufficient to stimulate an immune response against the antigen, e.g., a cancer antigen or antigen from an infectious pathogen, in the mammal. The compositions, vaccines and methods described herein can be utilized with any suitable subject, e.g., an animal such as a mammal (e.g., human beings, rodents, dogs, cats, goats, sheep, cows, horses, etc.). A human patient suffering from or at risk for developing a cancer or infectious disease is a typical subject.

Compositions and Methods for Delivering siRNA to PAPCs

Also described herein are compositions and methods for delivering an siRNA into a PAPC. In a typical embodiment, a composition for delivering an siRNA into a PAPC includes at least one at least one charged (e.g., positively-charged) polymeric carrier (e.g., a dendrimer) having conjugated thereto at least one MHC targeting and immunogenic peptide (e.g., a T helper peptide) and an siRNA. The at least one MHC targeting and immunogenic peptide (e.g., T helper epitope) and the siRNA are conjugated to the exterior surface of the at least one charged (e.g., positively-charged) polymeric carrier (e.g., dendrimer) such that the at least one T helper epitope specifically binds to PAPCs. The siRNA can be directed against (specific for) any gene of interest (e.g., Foxp3, CD-28, CTLA-4). The composition can further include a water-in-oil emulsion.

A typical method of delivering siRNA into PAPCs includes the steps of: providing a composition including at least one dendrimer having conjugated thereto at least one T helper peptide and at least one siRNA, wherein the at least one T helper peptide and the at least one siRNA are conjugated to the exterior surface of the dendrimer such that the at least one T helper peptide specifically binds to PAPCs; and administering the composition to a mammalian subject under conditions in which the at least one dendrimer having conjugated thereto at least one T helper peptide and at least one siRNA binds to a PAPC and the siRNA enters the PAPC and is expressed within the PAPC. The composition can further include a water-in-oil emulsion. In the method, the siRNA can be directed against (specific for) any gene of interest (e.g., FOXp3) to silence the expression of the gene of interest. In one example, siRNA directed against FoxP3 is used to silence expression of FoxP3, a molecule that results in induction of regulatory T cells, cells that suppress immune responses and act as a negative regulation of immune responses. This embodiment can find particular use for cancer therapy where regulatory T cells suppress immunotherapy and interventions. Regulatory T cells express MHC class II and can be targeted via PADRE-dendrimer or other CD4 epitope-dendrimer. Another example is CTLA-4 on CD4 T cells that transmits an inhibitory signal to T cells. In an embodiment wherein siRNA specific for CTLA-4 is complexed with a PADRE-dendrimer, the complex targets MHC class II expressing-cells including CD4 T cells and silences the CTLA-4 expression. The lower the expression of CTLA-4, the higher the immune responses against the pathogen or cancer, and when delivered into PAPCs, it prevents or reduces expression of molecules that inhibit immune responses (to enhance immune responses against pathogens, cancers, or when host is vaccinated) or enhances immune responses including B7.1, LFA-3, ICAM-1 (inducer of signal 2 needed for activation of T cells) for the therapy of autoimmune diseases such as Psoriasis.

In a typical embodiment, a composition described herein includes an siRNA specific to co-inhibitory and co-stimulatory molecules and their putative co-stimulatory receptor(s)) (e.g., Foxp3, CD28 CTLA-4). Sequence-specific siRNAs bind to a target nucleic acid molecule, inhibiting the expression thereof. siRNAs are effective in the treatment of abnormal cells, abnormal cell growth and tumors, including those tumors caused by infectious disease agents. Compositions for delivery of siRNA and methods of treatment thereof are provided.

Methods of constructing and using ribozymes, siRNA and antisense molecules are known in the art (e.g., Isaka Y., Curr Opin Mol Ther vol. 9:132-136, 2007; Sioud M. and Iversen P. O., Curr Drug Targets vol. 6:647-653, 2005; Ribozymes and siRNA Protocols (Methods in Molecular Biology) by Mouldy Sioud, $2^{nd}$ ed., 2004, Humana Press, New York, N.Y.). An "antisense" nucleic acid can include a nucleotide sequence which is complementary to a "sense" nucleic acid encoding a protein, e.g., complementary to the coding strand of a double-stranded cDNA molecule or complementary to an mRNA sequence. The antisense nucleic acid can be complementary to an entire coding strand of a gene of interest, or to only a portion thereof. In another embodiment, the antisense nucleic acid molecule is antisense to a "noncoding region" of the coding strand of a nucleotide sequence encoding a gene of interest (e.g., the 5' and 3' untranslated regions). Anti-sense agents can include, for example, from about 8 to about 80 nucleobases (i.e. from about 8 to about 80 nucleotides), e.g., about 8 to about 50 nucleobases, or about 12 to about 30 nucleobases. Antisense compounds include ribozymes, external guide sequence (EGS) oligonucleotides (oligozymes), and other short catalytic RNAs or catalytic oligonucleotides which hybridize to the target nucleic acid and modulate its expression. Anti-sense compounds can include a stretch of at least eight consecutive nucleobases that are complementary to a sequence in the target gene (i.e., gene of interest). An oligonucleotide need not be 100% complementary to its target nucleic acid sequence to be specifically hybridizable. An oligonucleotide is specifically hybridizable when binding of the oligonucleotide to the target interferes with the normal function of the target molecule to cause a loss of utility, and there is a sufficient degree of complementarity to avoid non-specific binding of the oligonucleotide to non-target sequences under conditions in which specific binding is desired, i.e., under physiological conditions in the case of in vivo assays or therapeutic treatment or, in the case of in vitro assays, under conditions in which the assays are conducted.

RNA Interference (RNAi) is a remarkably efficient process whereby double-stranded RNA (dsRNA, also referred to herein as siRNAs, for small interfering RNAs, or ds siRNAs, for double-stranded small interfering RNAs) induces the sequence-specific degradation of homologous mRNA in animals and plant cells (Hutvagner and Zamore, Curr. Opin. Genet. Dev., 12:225-232 (2002); Sharp, Genes Dev., 15:485-490 (2001)). In mammalian cells, RNAi can be triggered by duplexes of small interfering RNA (siRNA) (Chiu et al., Mol. Cell., 10:549-561 (2002); Elbashir et al., Nature, 411:494-498 (2001)), or by micro-RNAs (miRNA), functional small-hairpin RNA (shRNA), or other dsRNAs which are expressed in vivo using DNA templates with RNA polymerase III promoters (Zeng et al., Mol. Cell, 9:1327-1333 (2002); Paddison et al., Genes Dev., 16:948-958 (2002); Lee et al., Nature Biotechnol., 20:500-505 (2002); Paul et al., Nature Biotechnol., 20:505-508 (2002); Tuschl, T., Nature Biotechnol., 20:440-448 (2002); Yu et al., Proc. Natl. Acad. Sci. USA, 99(9):6047-6052 (2002); McManus et al., RNA, 8:842-850 (2002); Sui et al., Proc. Natl. Acad. Sci. USA, 99(6):5515-5520 (2002)).

The dsRNA molecules typically include 16-30, e.g., 16, 17, 18, 19, 20, 21, 22, 23, 24, 25, 26, 27, 28, 29, or 30 nucleotides in each strand, wherein one of the strands is substantially identical, e.g., at least 80% (or more, e.g., 85%, 90%, 95%, or 100%) identical, e.g., having 3, 2, 1, or 0 mismatched nucleotide(s), to a target region in the mRNA, and the other strand is identical or substantially identical to the first strand. Each strand can also have one or more overhanging (i.e., non-complementary) nucleotides, e.g., one, two, three, four or more overhanging nucleotides, e.g., dTdTdT.

The dsRNA molecules can be chemically synthesized, or can be transcribed in vitro from a DNA template, or in vivo from, e.g., shRNA. The dsRNA molecules can be designed using any method known in the art; a number of algorithms are known in the art, see, e.g., Tuschl et al., Genes Dev 13(24):3191-7 (1999), and many are available on the internet.

Negative control siRNAs typically have the same nucleotide composition as the selected siRNA, but without significant sequence complementarity to the appropriate genome. Such negative controls can be designed by randomly scrambling the nucleotide sequence of the selected siRNA; a homology search can be performed to ensure that the negative control lacks homology to any other gene in the appropriate genome. In addition, negative control siRNAs can be designed by introducing one or more base mismatches into the sequence. In some embodiments, siRNA can be produced using modified nucleotides (e.g., 2F-RNA) to make the siRNA resistant to nucleases.

Methods and Kits for Generating Antibodies

Compositions, kits and methods for generating antibodies that can be administered to a subject for therapeutic or prophylactic purposes are described herein. Current methods of DNA delivery into cells are inefficient, complex, and induce poor immune responses. The compositions and methods described herein, however, result in a strong antibody response that demonstrates rapid and high expression of an antigen of interest. The dendrimer/T helper peptide conjugates (e.g., PADRE-dendrimers) described herein can be complexed with (conjugated to) peptides or polypeptides or a nucleic acid (e.g., DNA) in a method of generating antibodies. Binding poly(I:C) to dendrimers is of particular use for the production of monoclonal antibodies because it reduces the frequency of and intervals between injections. In the experiments described below, delivery and expression of GFP in the cornea and skin as well as strong humoral responses were shown after a single injection of PADRE-dendrimer complexed with DNA. 50% of current drugs target membrane proteins that are the most difficult to purify. The compositions, kits and methods described herein provide tools to target such difficult-to-purify proteins without a need for purifying them.

Polyclonal antibodies are heterogeneous populations of antibody molecules that are contained in the sera of the immunized animals. Antibodies that can be produced using the compositions, kits and methods described herein therefore include polyclonal antibodies and, in addition, monoclonal antibodies, single chain antibodies, Fab fragments, $F(ab')_2$ fragments, and molecules produced using a Fab expression library. Monoclonal antibodies, which are homogeneous populations of antibodies to a particular antigen, can be prepared using the dendrimer/T helper epitope conjugates described herein and standard hybridoma technology (see, for example, Kohler et al., Nature 256:495, 1975; Kohler et al., Eur. J. Immunol. 6:511, 1976; Kohler et al., Eur. J. Immunol. 6:292, 1976; Hammerling et al., "Monoclonal Antibodies and T Cell Hybridomas," Elsevier, N.Y., 1981; Ausubel et al., supra). In particular, monoclonal antibodies can be obtained by any technique that provides for the production of antibody molecules by continuous cell lines in culture such as described in Kohler et al., Nature 256:495, 1975, and U.S. Pat. No. 4,376,110; the human B-cell hybridoma technique (Kosbor et al., Immunology Today 4:72, 1983; Cole et al., Proc. Natl. Acad. Sci. USA 80:2026, 1983), and the EBV-hybridoma technique (Cole et al., "Monoclonal Antibodies and Cancer Therapy," Alan R. Liss, Inc., pp. 77-96, 1983). Such antibodies can be of any immunoglobulin class including IgG, IgM, IgE, IgA, IgD and any subclass thereof. A hybridoma producing a mAb as described herein may be cultivated in vitro or in vivo. The ability to produce high titers of mAbs in vivo makes the compositions, kits and methods described herein particularly useful for mAb production.

The compositions, kits and methods described herein in which a dendrimer/T helper peptide (e.g., PADRE-dendrimers) is complexed with (conjugated or bound to) a nucleic acid encoding a protein or antigen negate the need for the purification of protein or antigen since the nucleic acid (e.g., plasmid DNA or mRNA) encoding the antigen or protein offer the advantages of i) elimination of tedious and/or costly and/or timely steps of protein purification, ii) the expression of the native form of the protein in vivo by cell machinery of the host which negates the challenge of a non-native form of the protein that results from conventional protein purifications, and ii) an ideal method for generation of therapeutic monoclonal antibodies where the natural/native form of the protein or antigen is the target.

Human antibodies against a particular antigen can be made by adapting known techniques for producing human antibodies in animals such as mice. See, e.g., Fishwild, D. M. et al., Nature Biotechnology 14 (1996): 845-851; Heijnen, I. et al., Journal of Clinical Investigation 97 (1996): 331-338; Lonberg, N. et al., Nature 368 (1994): 856-859; Morrison, S. L., Nature 368 (1994): 812-813; Neuberger, M., Nature Biotechnology 14 (1996): 826; and U.S. Pat. Nos. 5,545,806; 5,569,825; 5,877,397; 5,939,598; 6,075,181; 6,091,001; 6,114,598; and 6,130,314. Humanoid or humanized antibodies against a particular antigen can be made from non-human antibodies by adapting known methods such as those described in U.S. Pat. Nos. 5,530,101, 5,585,089, 5,693,761, and 5,693,762.

Once produced, polyclonal or monoclonal antibodies can be tested for specific antigen recognition by Western blot, immunoprecipitation analysis by standard methods or other suitable methods, for example, as described in Ausubel et al., supra. Antisera can be raised by injections in a series, preferably including at least three booster injections.

Antibody fragments that recognize and bind to specific epitopes can be generated by known techniques. For example, such fragments include but are not limited to F(ab')$_2$ fragments that can be produced by pepsin digestion of the antibody molecule, and Fab fragments that can be generated by reducing the disulfide bridges of F(ab')$_2$ fragments. Alternatively, Fab expression libraries can be constructed (Huse et al., Science 246:1275, 1989) to allow rapid and easy identification of monoclonal Fab fragments with the desired specificity.

A typical method of delivering an antigen to a mammal and inducing production of monoclonal antibodies against the antigen in the mammal for the purpose of obtaining monoclonal antibodies includes administering to the mammal a composition including at least one dendrimer having conjugated thereto at least one T helper peptide and a peptide or polypeptide antigen or a nucleic acid encoding the antigen wherein the at least one T helper peptide and the nucleic acid or peptide or polyeptide antigen are conjugated to the exterior surface of the at least one dendrimer such that the at least one T helper peptide specifically binds to PAPCs and the combination of the at least one T helper peptide, at least one dendrimer, and the nucleic acid or peptide or polypeptide antigen are able to induce an immune response against the antigen. In this method, the composition is administered in an amount effective to induce MHC class II mediated activation of helper T cells, resulting in production of monoclonal antibodies against the antigen. In a method of producing antibodies in mice, after the mice are immunized with antigen as described above, antibodies are harvested from one or more mice, and are screened for high titer. A mouse with high titer is selected, and the spleen from this mouse is removed. Fusion with myeloma is then performed, and screening for the best binding clone is performed.

Also described herein are kits for generating antibodies (e.g., monoclonal antibodies) to an antigen that eliminate the need for protein purification. A typical kit includes a container that includes a plurality of dendrimer/T helper peptide complexes (conjugates) as described herein (e.g., PADRE-derivatized dendrimers, dendrimers conjugated to influenza HA, etc.), and a physiological buffer, typically with a pH of 7.4. In one example of a buffer or medium, the buffer or medium includes Eagle's Minimal Essential Medium, buffered with HEPES and sodium bicarbonate, and supplemented with hypoxanthine, thymidine, sodium pyruvate, L-glutamine, and less than 10% serum bovine albumin or individual serum proteins including insulin and/or transferrin with 100 mg/L CaCl$_2$ where the endotoxin level is less than 1.0 EU/mL. In this embodiment, a user of the kit dilutes at least one nucleic acid (e.g., DNA plasmid) encoding one antigen with the buffer at 100-200 µl g/ml, and while shaking gently, adds the composition (T helper-dendrimer) to the diluted plasmid DNA. In a typical embodiment, a ratio of 10:1 of T helper-dendrimer to plasmid DNA is used (N:P), which is approximately 7 times (weight) of composition to one time (weight) of DNA plasmid(s). In one embodiment, the following conditions are followed. After 10 minutes incubation at room temperature, 100 ul of the mixture containing 10-20 µg of the plasmid(s)-DNA/composition is subcutaneously injected in mice. A similar booster in 14 days is followed by standard methods of primary screening, fusion and final screenings for monoclonal antibodies. In addition to nucleic acids, the compositions and kits described herein may be conjugated to proteins or antigens. In such an embodiment, typically the same ratio of 10:1 of the composition to protein results in the complex formation. The instructions for use included in a kit as described herein describes the protocol of making proper ratios, buffers, and optimization and troubleshooting when needed. Complexation of plasmid DNA or protein/antigen with the PADRE-dendrimer conjugates described herein is generally done by mixing the two components in aqueous solution buffered at physiological pH with a physiological buffer including PBS. Typical N/P (amine to phosphate) ratios are 10:1. Gel electrophoresis or other suitable assay can be used to demonstrate complete complexation of the DNA to the PADRE-dendrimer.

A kit as described herein can be used with any vector or plasmid encoding an antigen of interest. Instructional materials for preparation and use of the dendrimer/T helper eptiope complexes (conjugates) described herein are generally included. While the instructional materials typically include written or printed materials, they are not limited to such. Any medium capable of storing such instructions and communicating them to an end user is encompassed by the kits and methods herein. Such media include, but are not limited to electronic storage media (e.g., magnetic discs, tapes, cartridges, chips), optical media (e.g., CD ROM), and the like. Such media may include addresses to internet sites that provide such instructional materials.

Compositions and Methods for Delivering a Nucleic Acid to a Cell

In the experiments described herein, delivery of a gene encoding GFP was specifically delivered to MHC Class II cells (cells expressing MHC Class II) and expression of the gene was observed. Thus, the compositions and methods described herein may find use in any gene therapy application. A composition for delivering a nucleic acid to a cell typically includes at least one positively-charged highly branched polymeric dendrimer having conjugated thereto at least one T helper peptide and at least one nucleic acid encoding a peptide or protein, wherein the at least one T helper peptide and the nucleic acid are conjugated to the exterior surface of the at least one positively-charged highly branched polymeric dendrimer such that the at least one T helper peptide specifically binds to the cell, and the combination of the at least one T helper peptide, at least one positively-charged highly branched polymeric dendrimer, and the nucleic acid are internalized by the cell. A method of delivering a nucleic acid to a cell typically includes contacting the cell with a composition including at least one positively-charged highly branched polymeric dendrimer having conjugated thereto at least one T helper peptide and at least one nucleic acid encoding a peptide or protein, wherein the at least one T helper peptide and the nucleic acid are conjugated to the exterior surface of the at least one positively-charged highly branched polymeric dendrimer such that the at least one T helper peptide specifically binds to the cell, and the combination of the at least one T helper peptide, at least one positively-charged highly branched polymeric dendrimer, and the nucleic acid are internalized by the cell. In a typical embodiment, the peptide or protein is expressed within the cell.

Administration of Compositions

The vaccines and compositions described herein may be administered to mammals (e.g., dog, cat, pig, horse, rodent, non-human primate, human) in any suitable formulation. For example, a composition including a PADRE-dendrimer conjugated to siRNA or a vaccine including a PADRE-dendrimer complexed to a nucleic acid, or peptide or polypeptide antigen may be formulated in pharmaceutically acceptable carriers or diluents such as physiological saline or a buffered salt solution. Suitable carriers and diluents can be selected on the basis of mode and route of administration and standard pharmaceutical practice. A description of exemplary pharmaceutically acceptable carriers and diluents, as well as pharmaceutical formulations, can be found in Remington's Pharmaceutical Sciences, a standard text in this field, and in USP/NF. Other substances may be added to the compositions to stabilize and/or preserve the compositions.

The compositions and vaccines described herein may be administered to mammals by any conventional technique. Typically, such administration will be parenteral (e.g., intravenous, subcutaneous, intratumoral, intramuscular, intraperitoneal, or intrathecal introduction). The compositions may also be administered directly to a target site. The compositions may be administered in a single bolus, multiple injections, or by continuous infusion (e.g., intravenously, by peritoneal dialysis, pump infusion). For parenteral administration, the compositions are preferably formulated in a sterilized pyrogen-free form. In therapeutic applications, the compositions and vaccines described herein are administered to an individual already suffering from cancer, or infected with the pathogen (e.g., virus) of interest. In prophylactic applications, the compositions and vaccines described herein are administered to an individual at risk of developing (e.g., genetically predisposed to, or environmentally exposed to) cancer or an infectious disease (i.e., infected with a pathogen (e.g., virus) of interest).

In therapeutic applications, the compositions and vaccines described herein are administered to an individual already suffering from cancer, or infected with the pathogen (e.g., virus) of interest. In prophylactic applications, the compositions and vaccines described herein are administered to an individual at risk of developing (e.g., genetically predisposed to, or environmentally exposed to) cancer or an infectious disease (i.e., infected with a pathogen (e.g., virus) of interest).

Effective Doses

The vaccines and compositions described herein are preferably administered to a mammal (e.g., dog, cat, pig, horse, rodent, non-human primate, human) in an effective amount, that is, an amount capable of producing a desirable result in a treated mammal (e.g., prevention or elimination of cancer in a mammal, protection against infectious disease(s), etc.). Such a therapeutically effective amount can be determined as described below.

Toxicity and therapeutic efficacy of the vaccines and compositions described herein can be determined by standard pharmaceutical procedures, using either cells in culture or experimental animals to determine the $LD_{50}$ (the dose lethal to 50% of the population). The dose ratio between toxic and therapeutic effects is the therapeutic index and it can be expressed as the ratio $LD_{50}/ED_{50}$. Those compositions that exhibit large therapeutic indices are preferred. While those that exhibit toxic side effects may be used, care should be taken to design a delivery system that minimizes the potential damage of such side effects. The dosage of preferred compositions lies preferably within a range that includes an $ED_{50}$ with little or no toxicity. The dosage may vary within this range depending upon the dosage form employed and the route of administration utilized.

Therapeutically effective amounts of the compositions and vaccines described herein generally range for the initial immunization (that is for therapeutic or prophylactic administration) from about 1 µg to about 25,000 µg (e.g., 1, 100, 500, 2000, 2500, 10,000, 15,000, 25,000 µg) of a complex of T helper epitope/dendrimer conjugated to antigen or bound to a nucleic acid encoding the antigen for a 70 µg patient (e.g., 0.14 µg to 357 µg of plasmid(s) DNA or protein and 0.86 µg to 2142.85 µg of the T-helper-dendrimer), followed by boosting dosages of from about 1 µg to about 2500 µg of the complex (vaccine) pursuant to a boosting regimen over weeks to months depending upon the patient's response and condition by measuring specific CTL activity and/or antibody responses in the patient's blood. In one embodiment, 15 daily administrations of dendrimer in doses>133-fold greater then the above doses may be administered to a mammal with no toxicity (see Abhay Singh Chauhan et. al. 2009 Proc. R. Soc. A, 466, pp 1535-1550. 2009).

For treating a subject currently suffering from cancer or an infectious disease and/or who has just been diagnosed with cancer or an infectious disease, administration preferably begins at the first sign of disease or the detection or surgical removal of tumors or shortly after diagnosis in the case of acute infection. This is followed by boosting doses until at least symptoms are substantially abated and for a period thereafter. In chronic infection, loading doses followed by boosting doses may be required. For prophylactic use, administration may begin as soon as an individual becomes aware of a predisposition to cancer, or prior to an expected exposure to an infectious disease.

As is well known in the medical and veterinary arts, dosage for any one subject depends on many factors, including the subject's size, body surface area, age, the particular composition to be administered, time and route of administration, general health, and other drugs being administered concurrently. Dendrimers such as PAMAM have been tested in preclinical studies as well as in clinical trials. Recently, the FDA granted a "fast track" status to VivaGel® (Starpharma, Melbourne, Australia), already in phase III clinical trials. Therapeutic use of dendrimers in the cornea is known, and dendrimers have been used in corneal gene delivery. Examples of using dendrimers in corneal applications include the therapy of corneal neovascularization, photodynamic therapy, and tissue-engineering as a corneal equivalent. Poly(I:C) has been administered to humans for more than 40 years as a "natural" inducer of Interferon. Several recent clinical trials have examined different doses and routes of administration for safety and enhanced immunogenicity; general safety and enhanced immunogenicity have been repeatedly reported and established.

EXAMPLES

The present invention is further illustrated by the following specific examples. The examples are provided for illustration only and should not be construed as limiting the scope of the invention in any way.

Example 1—An Adjuvanted/Targeted Nanoparticle-Based Platform for Genetic Vaccination Therapy of Established Melanoma Tumors Genetic vaccination using naked DNA is used to produce antigens in their natural forms. However, the low in vivo transfection efficacy, a lack of effective delivery and the poor specificity of current genetic vaccination approaches strongly limit their efficacy. To overcome these limitations, a novel and flexible platform for antitumor DNA vaccination that 1) allows the specific and efficient transfection of PAPCs in vivo, 2) provides "danger signals" that result in maturation of autologous PAPCs and hence robust immune responses and, 3) activates helper T cells that further boost the generated immune responses was developed and is described herein.

The novel dendrimer-based nanoparticles described herein are typically prepared by the conjugation of two reactants: a fifth-generation, amino-terminated, PAMAM dendrimer, and a targeting/immune-enhancing peptide, or universal T helper Epitope (PADRE). The data described below showed this platform to i) achieve an objective anti-tumor effect with a reduction in tumor size of 50% of established and highly aggressive B16/LU8 melanoma tumors in C57BL mice, ii) induce a robust immune response against the product of the gene used in vaccination, and ii) increase transfection efficiency in both mouse and human APCs by 2- to 3-fold. Moreover, in vivo experiments using GFP-encoding plasmid conjugated to PADRE-dendrimer showed that GFP is produced in the draining lymph nodes.

Materials and Methods

PADRE-derivatized PAMAM dendrimer was generated as described above with the following modifications. The PADRE-dendrimer/DNA or siRNA complex was generated by incubation at room temperature for 10 minutes at a proper N/P ratio. Such complexes were added to primary PBMC or splenocytes for in vitro studies or injected subcutaneously for vaccination purposes. FIG. 1 shows PADRE decoration of (conjugation to) fifth-generation PAMAM Dendrimer.

To maintain the highly positively-charged surface for binding of multiple nucleic acids, one dendrimer molecule typically has two PADRE peptides conjugated to its surface so that it will still keep its positive net charge. Addition of PADRE to the dendrimers results in specific targeting of APCs, and strong CD4 help. The PADRE-derivatized PAMAM dendrimers not only escort plasmid-encoding antigens but also stimulate innate and adaptive immunity and act as a "danger signal."

Endotoxin-free MaxiPrep reagents were used to produce various plasmids (including pEGFP-C1, pMAX, GFP, TRP-2, P2, PCARD, and OVA in PCDNA3.1). Flourochrome-linked Immunosorbent Assays (FLISA), and Immuno Florescence Assays (IFA) were performed by standard methods. Briefly, transfected cos-7 cells were plated ($0.02 \times 10^6$ per well in a 96-well plate), cells were fixed and permeabilized. To measure mounted humoral responses, diluted sera were added to the wells and a secondary anti-mouse IgG-tagged with IRDye 800CW was used to measure antibody responses.

To prepare the Dendrimer/DNA complex, 1 µg/µL of prepared DNA in endotoxin-free PBS was complexed with dendrimer or dendrimer-PADRE in various charge ratios. After a 10 min incubation at room temperature, the complexes were added to cell culture or injected subcutaneously, intradermaly, or into the corneal stroma cavity.

For the vaccination of mice bearing B16-LU8 melanoma tumors, female C57BL mice in groups of five were implanted with ($0.02 \times 10^6$) B16-F10 cells, subcutaneously. Different groups received i) no treatment, ii) PCDNA3.1 (vector control) alone, iii) TRP-2 complexed with dendrimer alone, or iv) TRP-2 complexed with PADRE-dendrimer, on day two and ten post-tumor implantation. Tumor measurements were performed twice a week.

Results

The prepared PADRE-dendrimers were characterized. The peptide-dendrimer conjugate was made by simple amide coupling between the —COOH terminus of the peptide and the dendrimer amine groups. A 2:1 peptide/dendrimer challenge ratio was used in the reaction, seeking attachment of just a few peptides per dendrimer, in order to keep most of the free amine groups to develop large positive charges on the dendrimer. The product was purified by dialysis against pure water for at least 24 h and then dried under vacuum. The collected product, a clear oil, was characterized by 1H NMR, UV-Vis and MALDI-TOF mass spectroscopy. NMR shows large peaks corresponding to the dendrimer protons and a small set of peaks for the peptide protons. The MALDI-TOF mass spectrum of the PADRE-dendrimer conjugate shows a peak at a m/z ratio ca. 3,000 units higher than the peak observed for the dendrimer on its own. The excess mass corresponds to approximately 2 peptide epitopes (FIG. 17).

Figure 2:
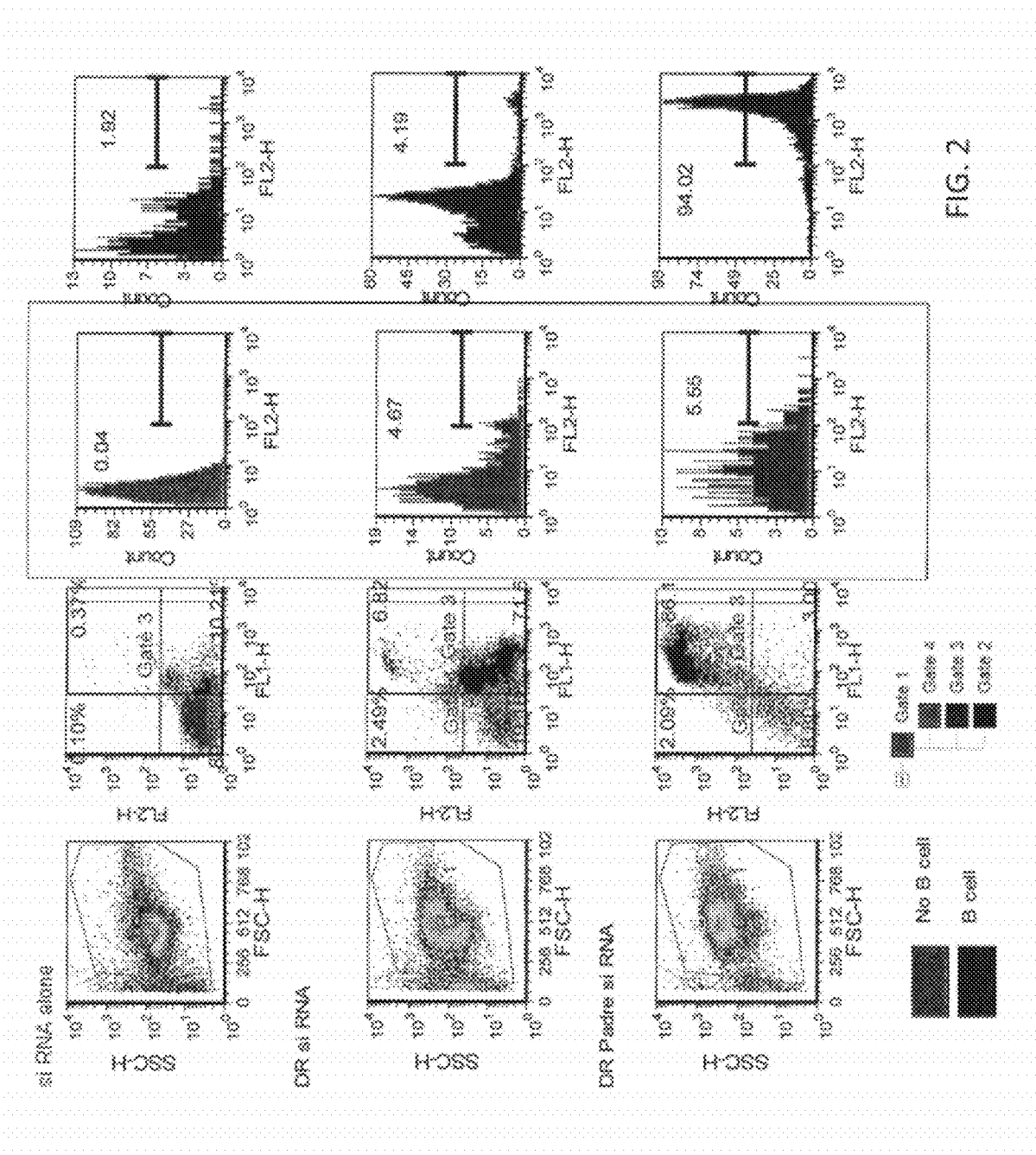
FIG. 2 is a series of dot plot flow cytometry images of analysis of human B cells showing in vitro delivery of PADRE-dendrimers complexed with a short nucleic acid sequence tagged with a red fluorochrome. This nucleic acid is a red-labeled dsRNA oligomer designed for use in RNAi analysis to facilitate assessment and optimization of siRNA oligonucleotides delivery into mammalian cells. Cells were co-cultured with the PADRE-dendrimers/multinucleotide complexes or controls for 4 hours after which the media was removed and fresh media was added. The images show the delivery of dsRNA oligomer tagged with Alexa Fuor into purified Human B cells. The lowest image in the fourth column of images shows the delivery of the oligo in approximately 92% of cells.
Figure 17:
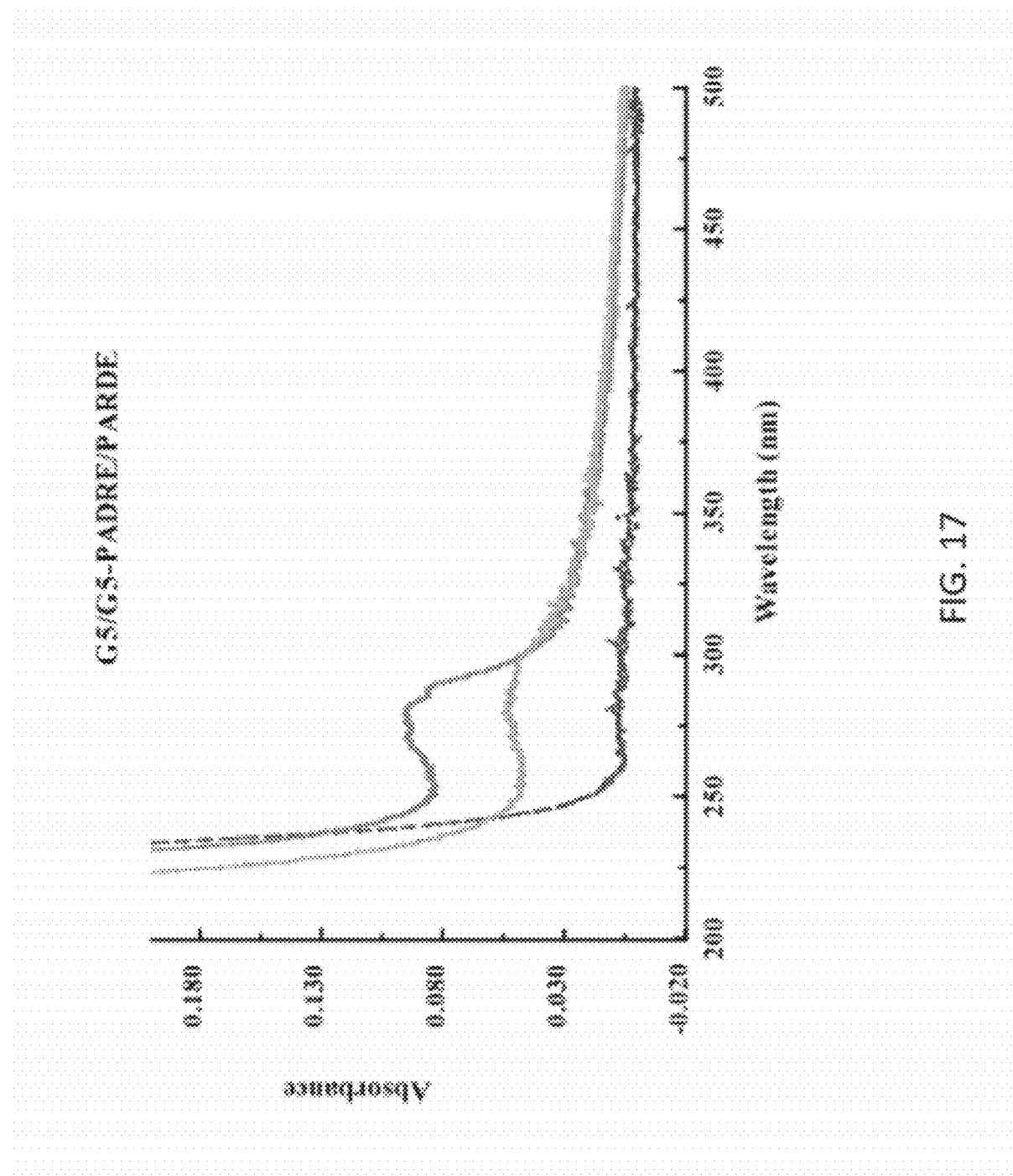
FIG. 17 is a graph showing UV-visible spectra of G5 dendrimer, conjugate, and peptide.

The data established that an average of two PADRE are present on each dendrimer (FIG. 17). In vitro delivery of multiple nucleic acids into autologous APCs was shown. In vitro multinucleotide delivery/transfection of human primary peripheral mononuclear cells was best achieved in the charge ratios of 1:5 and 1:10. FIG. 2 shows siRNA delivery (~%86) via PADRE-dendrimers into purified human B cells where Alexa Fluor-tagged siRNA complexed with (conjugated to) PADRE-dendrimer was incubated with B cells for 4 hours. Cells were stained with CD19/FITC and the red channel (PE) represents cells with the siRNA/Alexa Fluor.man Referring to FIG. 3, in vivo DNA delivery of PADRE-dendrimers was shown. Plasmids encoding GFP or TRP-2 were injected alone or complexed with PADRE-dendrimer, or dendrimer (i.e., dendrimer not complexed with PADRE). The images show the expression of GFP in skin (left) and cornea (right) 24 and 16 hours post-injection. Effective expression of GFP is demonstrated in both skin and cornea 24 and 16 hours post-injection of PADRE-dendrimer complexes. Targeting of the lymph nodes in vivo was demonstrated. Eight days after PADRE-dendrimer/GFP-plasmid complexes were injected subcutaneously (5 µg total plasmid), the adjacent lymph node was removed and compared with lymph nodes of a mouse injected with GFP-DNA alone. Fluorescent microscope images were taken on meshed lymph nodes on day eight post-immunization. Expression of antigen in the lymph node adjacent to the injection site was seen, but expression of antigen in a control lymph node was not seen.

Targeting of the lymph nodes in vivo was demonstrated. Eight days after PADRE-dendrimer/GFP-plasmid complexes were injected subcutaneously (5 µg total plasmid), the adjacent lymph node was removed and compared with lymph nodes of a mouse injected with GFP-DNA alone. Fluorescent microscope images were taken on meshed lymph nodes on day eight post-immunization. Expression of antigen in the lymph node adjacent to the injection site was seen, but expression of antigen in a control lymph node was not seen.

As shown in FIG. 4, specific immune responses were mounted after administration of PADRE-dendrimer/plasmid complexes. Strong humoral responses were observed upon one (GFP) or two immunizations (OVA) with complexes of plasmid/PADRE-dendrimer.

Figure 5:
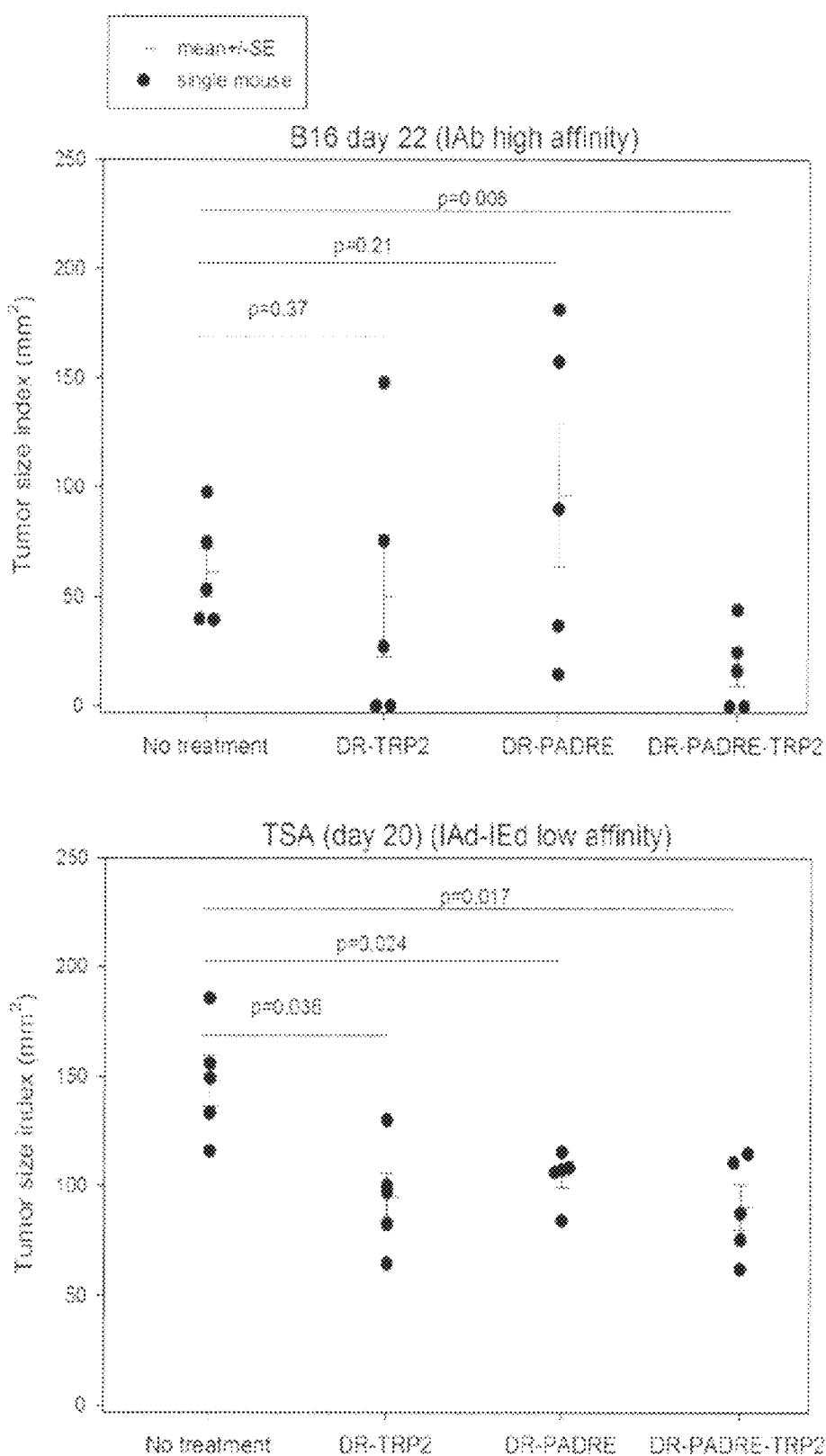
FIG. 5 is a pair of graphs showing PADRE-dendrimer therapy of established tumors. Mice implanted with B16 melanoma cells (top) or TSA (bottom) were vaccinated on day two or three post-tumor implantation followed with booster immunizations after a week.

The data shown in FIG. 5 shows PADRE-dendrimer therapy of established tumors. B16 melanoma is known to be an aggressive mouse tumor model. Mice implanted with B16 melanoma cells (top) or TSA (bottom) were vaccinated on day two or three post-tumor implantation followed with booster immunizations after a week. Follow up of tumor measurements clearly demonstrated that administration of the PADRE-dendrimers resulted in a protective immune response, in particular, in C57BL (lab) which has higher affinity for PADRE binding. C57BL also responds stronger to PADRE via induction of T helper cells.

Referring to FIG. 5, the results demonstrated an objective anti-tumor effect with a reduction in tumor size of 50% of the highly aggressive and established B16/LU8 tumor. This aggressive model was chosen intentionally to show the potency of the platform as everything else fails. The delay in tumor growth and reduction in tumor size is unprecedented. Indeed, on day 22 post-tumor implantation, no or no palpable tumors were detected in the test group (i.e., those animals receiving a vaccine as described herein) which was significantly different from all control groups. The amount of DNA used in this vaccination (vaccine dose) was much lower than what is normally used (20 μg and a total of 2 immunizations). In FIG. 5, the lower figure is a negative control using Balb/c mice where PADRE does not bind properly, a similar experiment in a Balb/c TSA tumor model shows no efficacy. This clearly shows the specificity of the delivery system via MHC class II.

These data clearly demonstrate that the targeted adjuvanted nanopatricle platform described herein results in gene delivery, robust expression of the encoded antigen, antigen presentation, and induction of protective immune responses. Thus, the PADRE-dendrimer nanoparticles described herein are a novel and powerful adjuvanted/targeted delivery tool and platform for: i) protein-free generation of (monoclonal) antibodies, ii) immunological treatment/prevention of malignancies and infectious diseases with deceptive imprinting, and iii) delivery of siRNA for many immune-based therapeutic interventions.

Example 2—In Vitro Targeted Delivery and Transfection Efficiency

Figure 6:
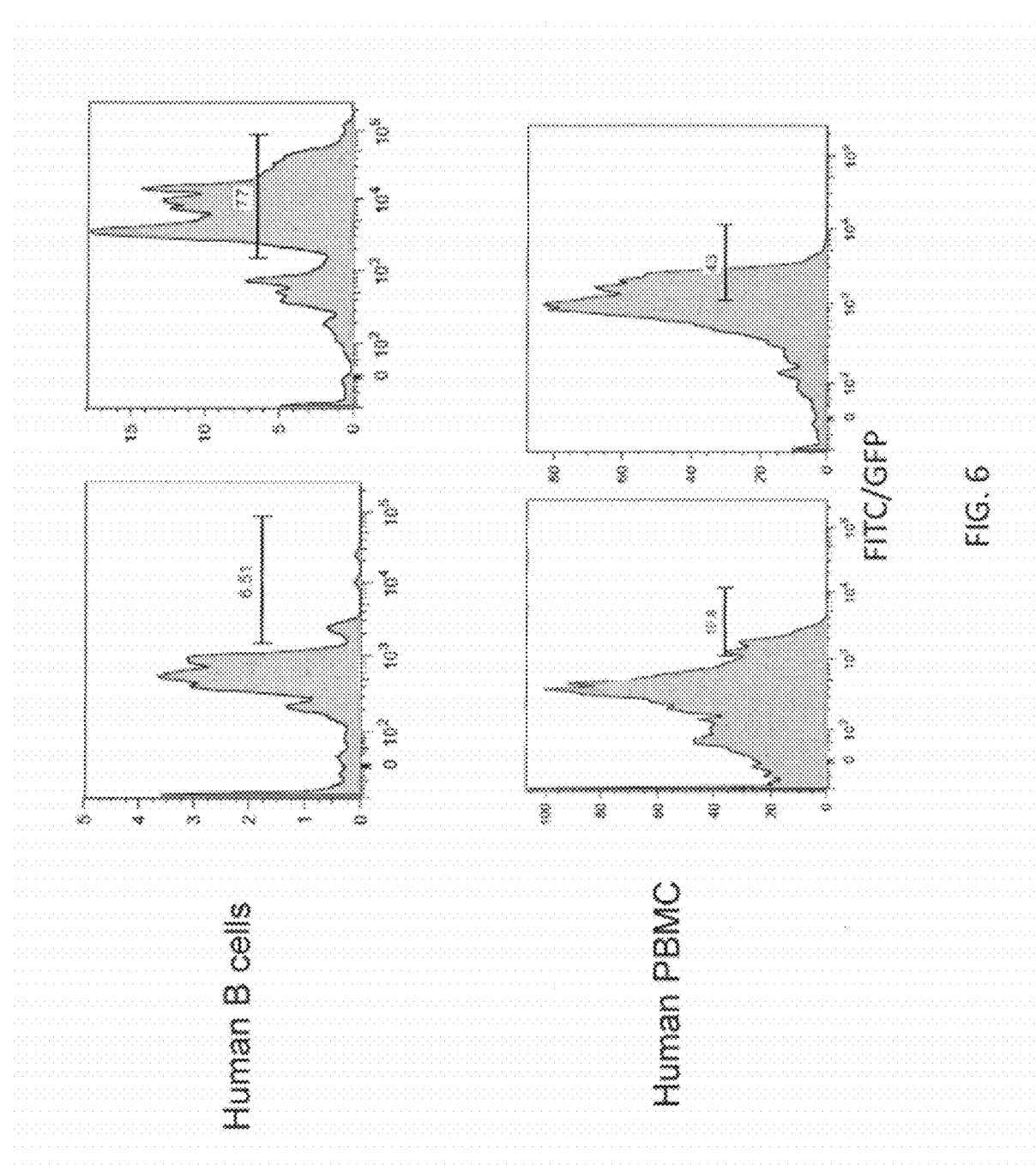
FIG. 6 is a series of flow cytometry histograms showing the expression of GFP in human peripheral blood mononuclear cells (PBMC), lower panel, and in human B cells, upper panel, upon co-culturing GFP plasmid (5 µg) complexed with Dendrimer-PADRE. Dendrimer/GFP-plasmid complex was used as a control, left histograms.

Referring to FIG. 6, in vitro targeted delivery of PBMCs results in 77% B cell transfection efficiency. Human PBMC from healthy donors were obtained. PBMCs were cultured at 6 million cells per ml of RPMI media with 10% fetal bovine serum. The plasmid encoding for GFP at 5 μg was diluted in 100 ul of a physiological buffer, PBS, and 5 μg of PADRE-dendrimer in 50 ul PBS was added to DNA while shaking. After 10 minutes incubation at room temperature, the mixture/complex of the GFP plasmid and PADRE-dendrimer was then added to PBMC. Twenty-four hours post incubation at 37° C./5% $CO_2$ incubator, PBMCs were stained with CD19 PE and cells were analyzed by flow cytometry. The expression of GFP was observed in 43% of total PBMC while when gated on B cells 77% of B cells expressed GFP. Control groups, PBMC incubated with same ratios of dendrimer and GFP plasmid showed about 11% and 7% GFP expression in total PBMC or B cells. No major viability change was observed when compared with PBMC with only media. This is a representative experiment of several. These experiments demonstrate i) the delivery of GFP plasmid into PBMC and in particular to MHC class II expressing cells (B cells), and ii) the expression of the GFP by PBMC and in particular by B cells.

Figure 7:
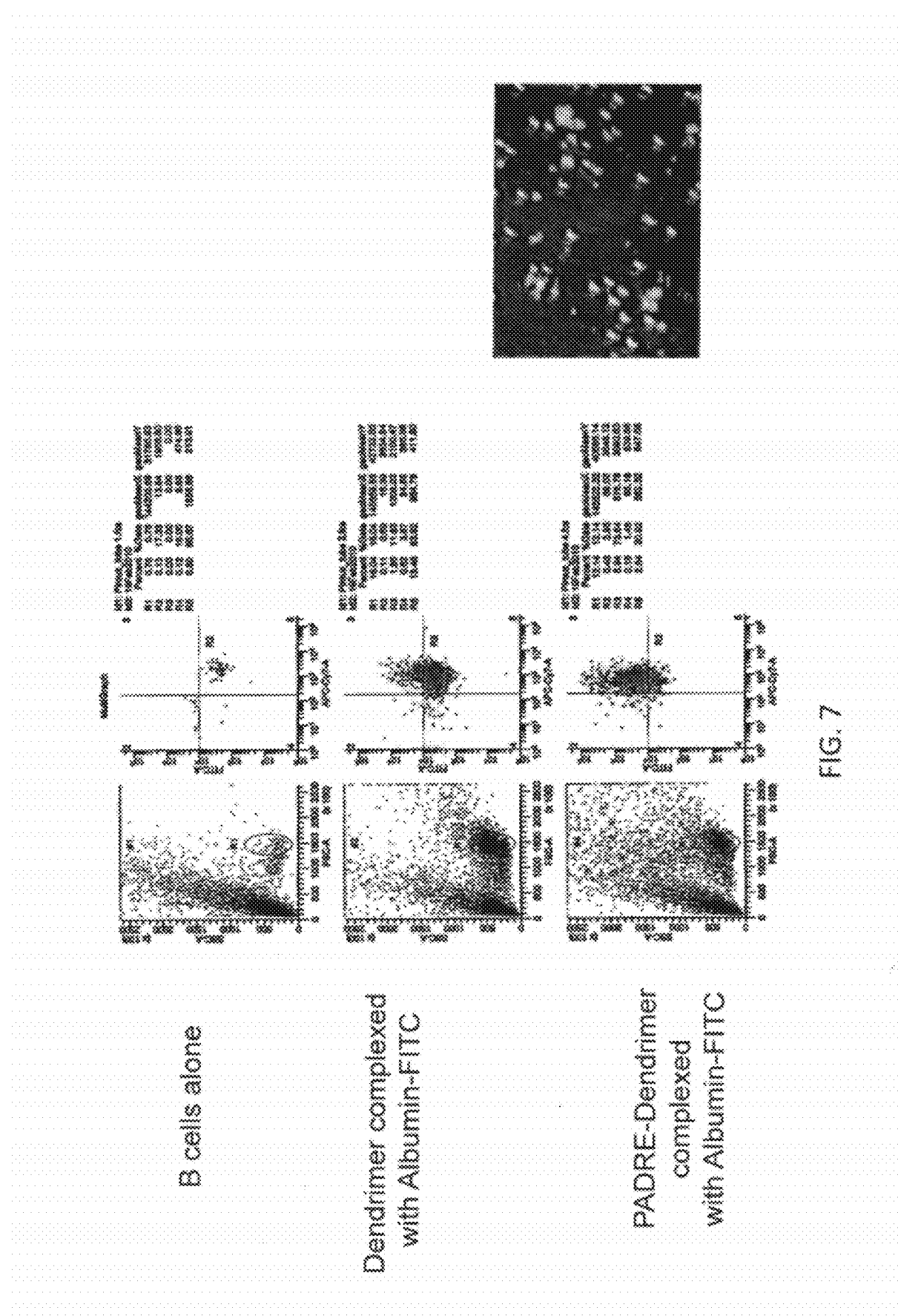
FIG. 7 is a series flow cytometry dot plots showing the in vitro delivery of a protein, Albumin-FITC, into human B cells by PDD. The left images show PDD/Albumin-FITC delivery into purified human B cells. Human purified B cells were collected and were co-cultured with PDD/Albumin-FITC. The left histograms show the delivery of Albumin-FITC in human B cells the morning after the PDD/Albumin-FITC added to human B cells. The Top histogram shows B cells alone, the histogram in the Middle shows the Dendrime/Albumin-FITC complex plus B cells and the lower histogram depicts the results of PDD/Albumin-FITC complex added to human B cells. The right picture is the image of fluorescent microscope of Albumin uptake by B cells one-hour post addition of PDD/Albumin-FITC complex.
Figure 9:
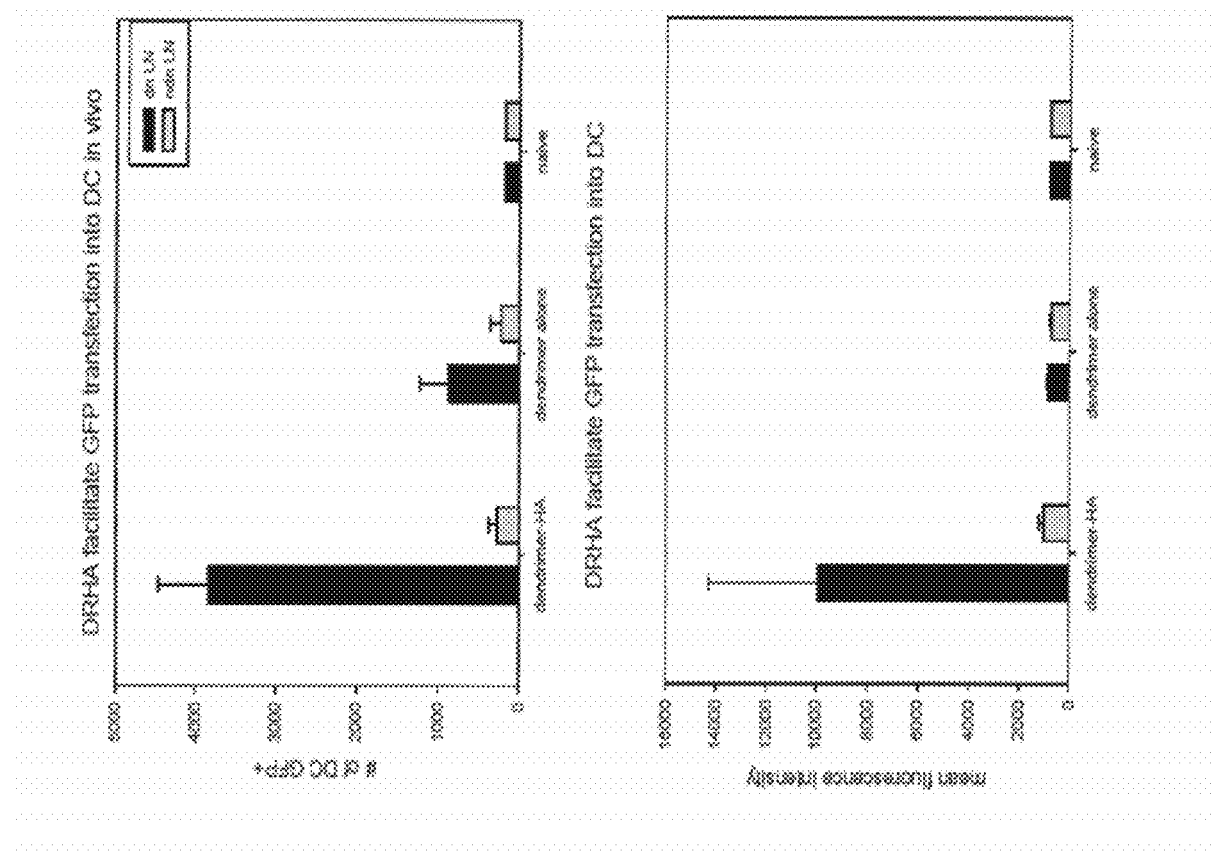
FIG. 9 is a pair of graphs showing that DRHA, a dendrimer decorated with a different T helper epitope, in vivo targeting DCs in the lymph node shows that DRHA facilitates GFP transfection into DCs. This experiment is similar to the one described in FIG. 8 with the difference that Balb/c mice have been used in conjunction with dendrimer conjugated with Iad-restricted HA peptide. The lymph node adjacent to the DRHA/GFP-plasmid or Dendrimer/GFP-plasmid injection site and a naïve lymph node were removed on day 5 post-injection of DRHA/GFP-plasmid or Dendrimer/GFP-plasmid. The charts show the results of the flow cytometry analysis of data obtained from cells of the lymph node after staining with CD11c (DC marker) for DC. The top pane shows the number of DC positive for GFP found draining lymph nodes of mice treated as indicated. The lower panel shows the mean fluorescence intensity of GFP within the DC. These results clearly indicate not only that DRHA augment the number of DC transfected in vivo but, also the number of plasmid molecules that get into the cells.

Example 3—Delivery of Peptides/Proteins into Mouse DCs In Vivo and Human B Cells In Vitro PDD/Albumin-FITC was delivered into purified human B cells (FIG. 7). Referring to FIG. 8, this Figure shows PADRE-dendrimer targeting of and efficacy in mouse DCs in vivo and a timeline for injection and lymph node analysis. The results of this experiment show that i) (FIG. 7) Albumin-FITC, a protein, mixed with PADRE-dendrimer was delivered in human B cells in less than two hours, ii) (FIG. 8) in day 5 post subcutaneous injection, PADRE, an epitope, conjugated to dendrimer was delivered into lymph node's B cells and DCs in vivo (the PADRE-dendrimer was complexed to GFP-plasmid to visualize the delivery of the complex to lymph node/B cells/DCs.), iii) (FIG. 9) in day 5 post subcutaneous injection, HA helper epitope of influenza, an epitope, conjugated to dendrimer was delivered into lymph node's DCs in vivo (the PADRE-dendrimer was complexed to GFP-plasmid to visualize the delivery of the complex to lymph node DCs). These data were representative of several experiments and in some the lymph nodes were removed on day 3 post subcutaneous injection of PADRE-dendrimer or HA-dendrimer each complexed with GFP plasmid. These results establish examples of the delivery to APCs including B cells and DC of a protein conjugated with FITC via FITC visualization of FITC as well as the delivery of two peptides, PADRE and HA helper epitopes conjugated to dendrimer where GFP plasmid was complexed with the peptide-dendrimer to facilitate visualization and analysis of the complex (peptide-linked to dendrimer complex with GFP-encoding plasmid) in the cells of lymph nodes. Specific in vitro and in vivo transfection of DCs was shown by in vivo flow cytometry data on targeting and expanding DCs in an adjacent lymph node, 5-days post-injection of the nanoparticle (PADRE-dendrimer/GFP-encoding plasmid) vs. controls (78% vs. ~7% GFP expression). The PADRE-derivatized dendrimer (PDD) enhances delivery due to its assisted opsonized effect of PADRE which with high affinity binds to MHC class II expressed on APC. Similarly, HA-dendrimer (DRHA)/GFP-plasmid was delivered in vivo in the neighboring lymph nodes, when injected subcutaneously (FIG. 9). Note that in mice, PADRE binds the MHC class II of IAb (C57BL mice) (FIG. 8) while selected HA epitope binds the MHC class II of IAd (Balb/c mice) (FIG. 9). The feasibility of in vivo delivery in two different mice strains with two different epitopes with similar results have been shown. The APC-targeted delivery resulting in the expression of GFP by PADRE-dendrimer/GFP-plasmid into human PBMCs (FIG. 6), purified human B cells (FIG. 6), and in splenocytes of C57BL mice, and the delivery of PADRE-dendrimer/dsRNA into human B cells (FIG. 10) and of monkey PBMC (FIG. 11) are additional in vitro evidence of the delivery of peptide to PAPCs by the compositions described herein. Because use of two different targeting peptides, whose unique feature is to bind to the MHC class II, works as shown in the experiments described herein, the vaccines, methods and compositions described herein encompass all MHC class II binding peptides. Referring to FIG. 9, dendrimer conjugated to influenza HA helper epitope (HDD) was also prepared. HDD may be used in balb/c mice. When injected into mice, HDD targets DCs in the adjacent lymph node.

Figure 10:
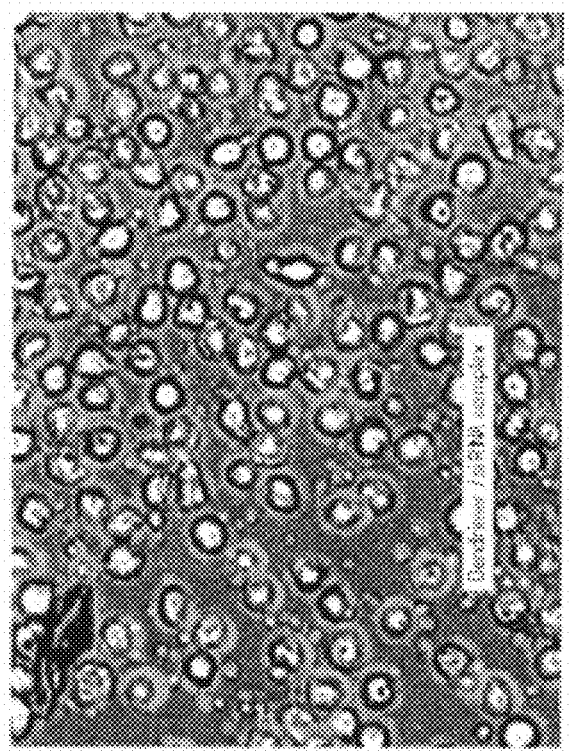
FIG. 10 is a micrograph of human B cells transfected with PADRE-dendrimer complexed with a red(Alexa Fluor)-labeled dsRNA oligomer oligo

Example 4—PADRE-Dendrimer Delivery of siRNA into Human B Cells and Non-Human Primate PBMCs and PADRE-Dendrimer Delivery of Plasmid into Non-Human Primate PBMCs Referring to FIG. 10, PADRE-dendrimers complexed to dssiRNA (a control siRNA) exhibited targeted delivery in vitro. 0.1 µg of dsRNA was diluted in 100 ul of PBS and 0.7 µg of the PADRE-dendrimer in 20 ul was added to dsRNA-Alexa Fluor tagged while shaking. The complex after a 10 minute incubation at room temperature was added to one million purified B cells (in RPMI plus 10% fetal bovine serum) in wells of a 24-well plate. About an hour post incubation at 37° C./5% $CO_2$ incubator, cells were washed and placed back in the wells (in 1 ml of fresh RPMI plus 10% fetal bovine serum) and were analyzed under fluorescent microscope in red channel. The overlay image of cells under bright field and red channel demonstrates the uptake of Alexa Fluor tagged dsRNA by human B cells (FIG. 10). Cells were incubated overnight at 37° C./5% $CO_2$ incubator when they were stained with CD19 (a B-cells marker) and analysed by flow cytometry (FIG. 2). As shown in the FIG. 2, >80% of the B cells were positive for Alexa Fluor (tagged to dsRNA) versus about 6% for the control, dendrimer/dsRNA-Alexa Fluor. These results clearly demonstrate the robust delivery of nucleic acids to PAPC by PADRE-dendrimer.

Figure 11:
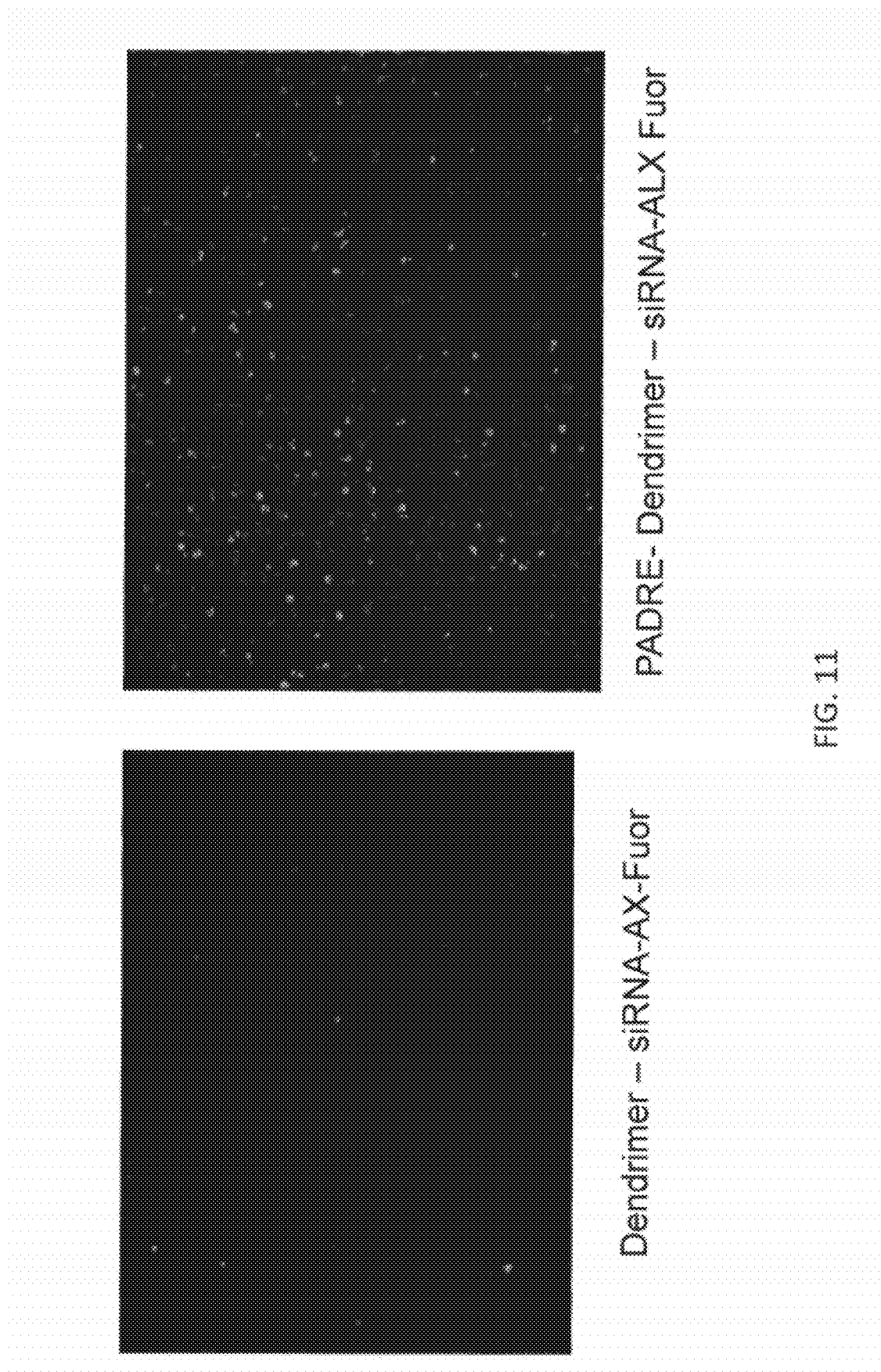
FIG. 11 is a pair of micrographs of PBMC of Baboon transfected with dendrimer complexed with a red(Alexa Fluor)-labeled dsRNA oligomer (left panel) and cells transfected with PADRE-dendrimer complexed with a red(Alexa Fluor)-labeled dsRNA oligomer (right panel). The flurescent microscope images were taken two hours post addition of PDD/dsRNA-Alexa-Fluor or control complex to Baboon PBMC. The image shows high efficacy of targeted delivery of multinucleutides to PBMC of monkey via PDD.
Figure 12:
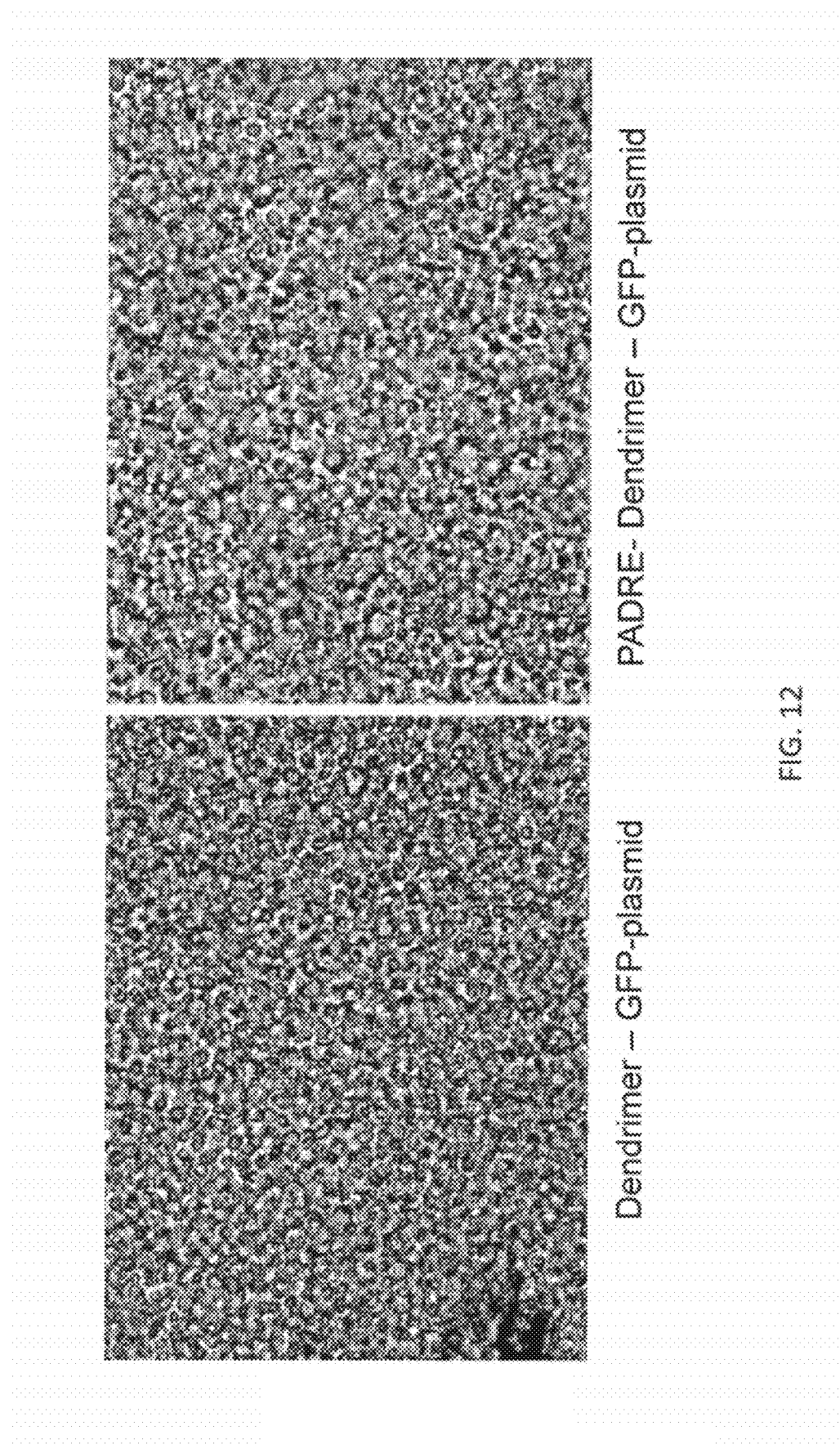
FIG. 12 is a pair of micrographs of Baboon PBMC transfected with dendrimer complexed with GFP-encoding plasmid (left panel) and cells transfected with PADRE-dendrimer complexed with GFP-encoding plasmid (right panel). PBMC of Baboon transfected with dendrimer complexed with GFP-plasmid (left panel) and cells transfected with PADRE-dendrimer complexed with GFP-plasmid (right panel). The flurescent microscope images were taken one day post addition of PDD/GFP-plasmid or control complex to Baboon PBMC. The image shows high efficacy of targeted delivery of the plasmid and the expression of the gene encoded by the plasmid via PDD.

PBMCs one sample from baboon (papio hamadryas), and two different samples from cynomolgus monkeys (macaca fascicularis) were tested. Fluorescent microscope images shown in FIG. 11 are representative, taken two hours post-addition of PADRE-dendrimer or dendrimer, each complexed with siRNA/Alexa Fluor. Similarly, PADRE-dendrimer or dendrimer complexed with GFP-plasmid were added to the PBMCs and were analyzed 24 hours after incubation (FIG. 12). The results show that, in less than 2 hours, PADRE-dendrimer delivers nucleic acids into the monkeys' PBMCs, while dendrimer shows only a modest delivery. These results strongly suggest that PADRE-dendrimer works on non-human primates.

Figure 13:
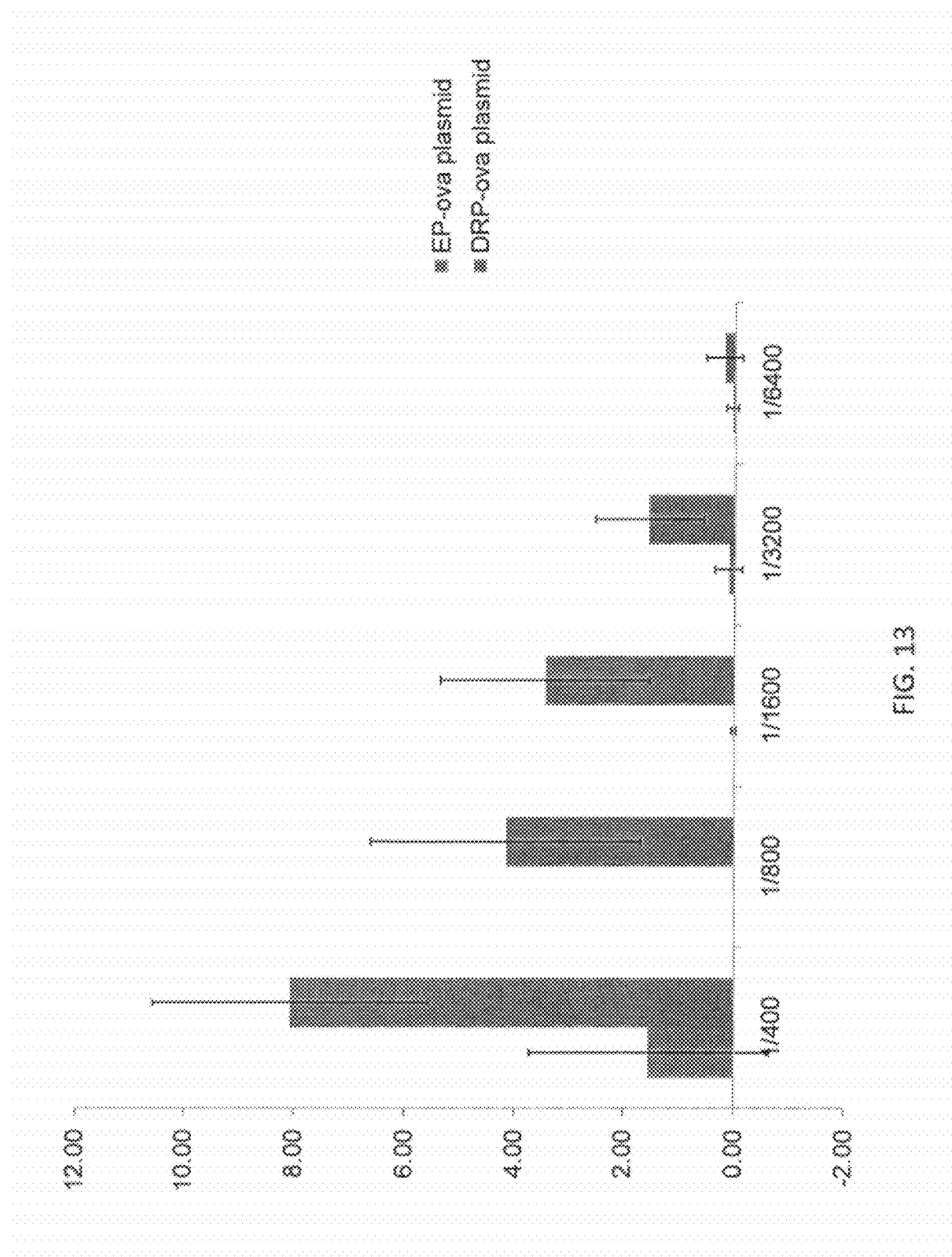
FIG. 13 is a graph of results showing that a single DNA vaccination with PADRE-Dendrimer complexed with plasmid (DRP-ova plasmid) is superior to in vivo electroporation of plasmid (EP-ova plasmid).

Example 5—Comparison of PADRE-Dendrimer Nanoparticles and the IN-CELL-ART™ Platform The PADRE-dendrimers described herein provide specific targeting of PAPCs in contrast to IN-CELL-ART's non-specific delivery to all cells. The IN-CELL-ART™ platform includes a 704 polymer that delivers DNA to cells via electroporation with no specific built-in adjuvant activity or any ligand for binding APCs. Currently, in vivo electroporation is known as the best non-viral genetic immunization method. The PADRE-dendrimers described herein provide induction of helper T cells that is not provided by the IN-CELL-ART's platform. In the experiments described above, the PADRE-dendrimers were shown to be efficacious in a therapeutic tumor model while IN-CELL-ART's has not been shown to be efficacious in an in vivo tumor model. In the experiments described herein, as a robust control, PADRE-dendrimers were compared with in vivo electroporation (FIG. 13). In contrast, IN-CELL-ART has only shown a comparison with naked DNA. A single immunization of the PADRE-dendrimers described herein was compared with in vivo electroporation for mounting humoral responses. To perform this experiment, PADRE-dendrimers were mixed with 5 µg of the plasmid at room temperature, and 10 minutes later, the mixture was injected into mice subcutaneously. Mice immunized with PADRE-dendrimers conjugated to OVA-encoding plasmid and control mice were challenged with 50 k B16F10-expressing OVA on day 28 post a single vaccination. All mice that received PADRE-dendrimers conjugated to plasmid were protected on day 25 post-tumor implantation versus 40% of those receiving plasmid via in vitro electroporation and 0% in the control group that received DNA only. As shown in FIG. 13, the results show that a single DNA vaccination with PADRE-dendrimer/plasmid (DRP-ova) is superior to in vivo electroporation (EP) delivery of plasmid (EP-ova) for induction of an anti-ova antibody humoral response.

Example 6—PADRE-Dendrimers Induce Strong Humoral Responses in Mice

Figure 14:
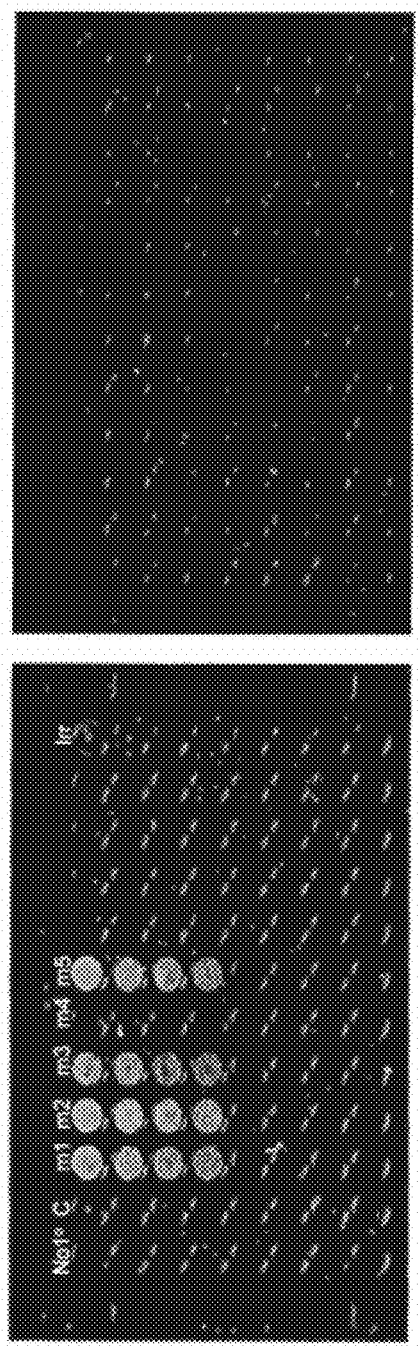
FIG. 14 is pair of photographs of multi-well plates upon in-cell Western assay using sera of immunized mice showing induction of high titres antibody responses in mice upon two immunizations with PDD/plasmid-PCARD antigen. Multi-well plates containing cos-7 cells transfected with plasmid encoding antigen (left panel) and cos-7 cells transfected with a control plasmid (right panel).
Figure 15:
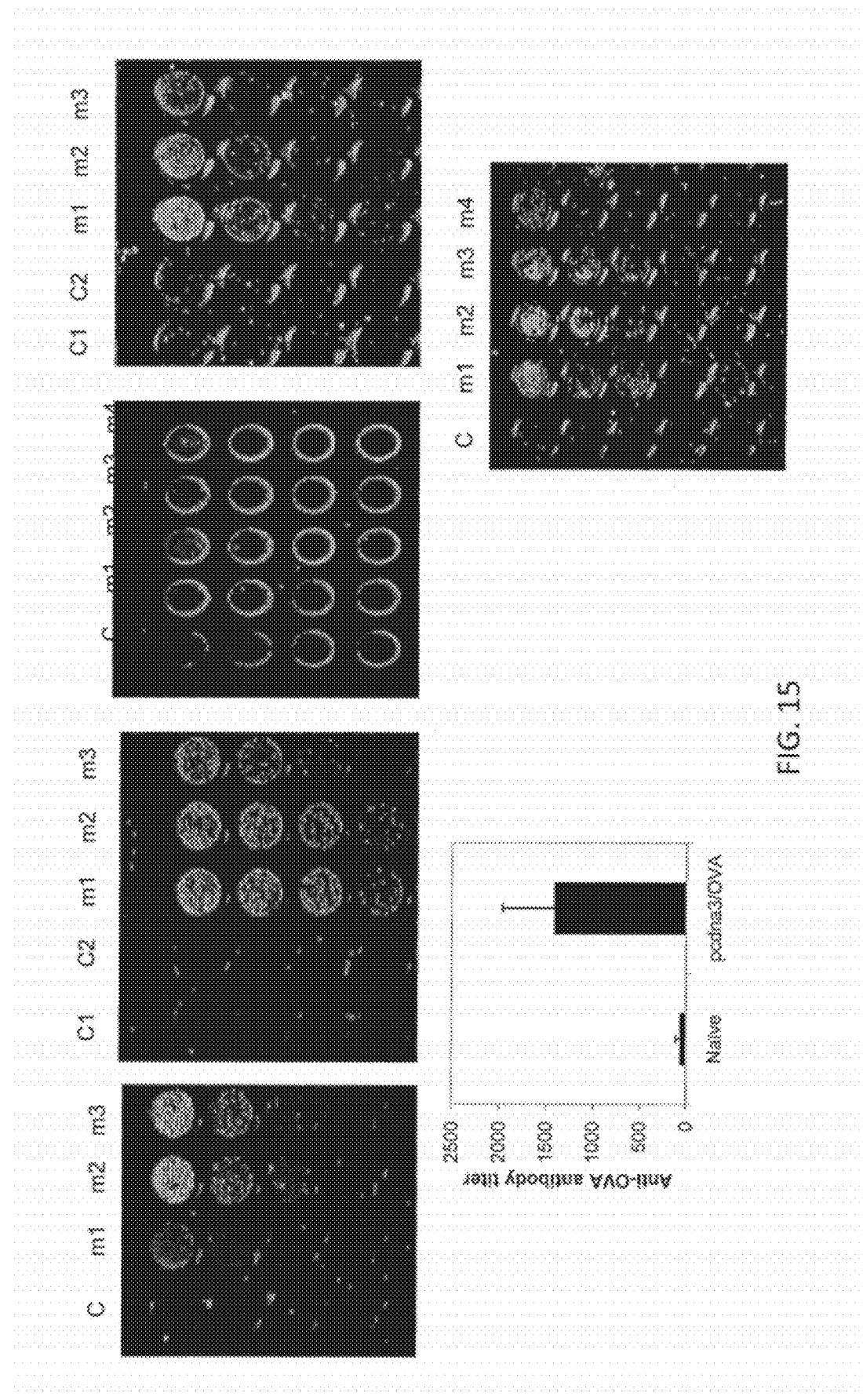
FIG. 15 is a graph and a series of photographs of multi-well plates upon in-cell Western assay using sera of immunized mice showing induction of high titres antibody responses in mice upon two immunizations with PDD/plasmid. Also shown are results from an in-cell Western FLISA after one immunization with PADRE-dendrimers complexed with plasmids encoding either GFP or ova or two immunizations with PADRE-dendrimers complexed with plasmids encoding CCR5, vgPCR, CathL, or p2.

As shown in FIGS. 14-16, PADRE-dendrimers complexed with a plasmid elicited strong humoral responses in mice.

Figure 18:
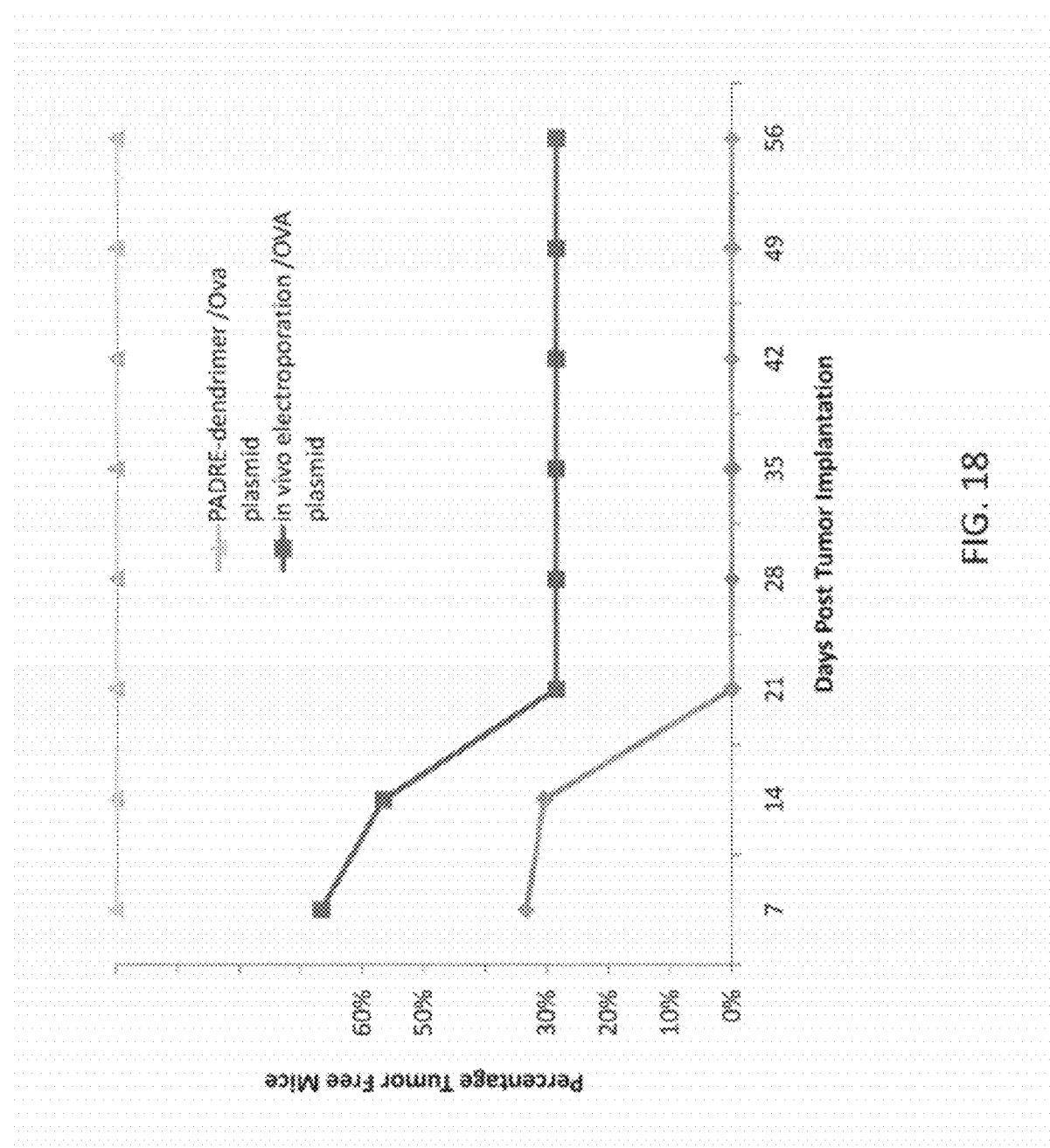
FIG. 18 is a graph showing eradication of B16/OVA tumors in a prophylactic setting by a vaccine as described herein (PADRE-dendrimer/OVA plasmid).

Example 7—Eradication of B16/OVA Tumors in a Prophylactic Setting by PADRE-Dendrimer/OVA Plasmid Vaccine Female C57BL mice, 6 weeks-old, in groups of five per cage received i) nothing, ii) two immunizations of 20 µg OVA-plasmid via "in vivo electroporation" using Derma Vax electroporator, or iii) two immunization with PADRE-dendrimer/OVA-plasmid (20 µg each). Immunizations were performed 2 weeks apart. Ten days post immunizations, all mice received subcutaneous injections (implantation) of 50,000 B16/OVA tumor cells in 100 µl PBS in the right flanks. Tumor measurements were performed twice a week and weekly data was plotted and is shown in FIG. 18. Two vaccinations with PADRE-dendrimer/20 µg OVA-plasmid resulted in complete eradication of B16/OVA tumors in all immunized mice while 100% of no treatment and 60% of mice vaccinated via "in vivo electroporation" remained tumor-bearing. All tumor bearing mice with tumors larger than 15% of the body weight were sacrificed.

Other Embodiments

Any improvement may be made in part or all of the compositions, kits, and method steps. All references, including publications, patent applications, and patents, cited herein are hereby incorporated by reference. The use of any and all examples, or exemplary language (e.g., "such as") provided herein, is intended to illuminate the invention and does not pose a limitation on the scope of the invention unless otherwise claimed. For example, although the experiments described herein involve eradication of B16 melanomas and induction of strong humoral responses to GFP, OVA, PCARD, CCR5, vgPCR, muPAR, CathL, or p2 antigens, the vaccines, compositions and methods described herein can find use in a number of other therapeutic and prophylactic applications, including preventing or eradicating additional types of cancer, and inducing an immune response and thus immunity against any antigen of interest (e.g., antigens from infectious pathogens). In another example, the vaccines, compositions and methods described herein can be used to deliver a protein or peptide that is not an antigen to a cell. In this example, a typical composition for delivering a peptide or protein to a cell includes at least one charged highly branched polymeric dendrimer having conjugated thereto at least one T helper peptide and at least one peptide or protein, wherein the at least one T helper peptide and the at least one peptide or protein conjugated to the exterior surface of the at least one charged highly branched polymeric dendrimer such that the at least one T helper peptide specifically binds to the cell. Any statement herein as to the nature or benefits of the invention or of the preferred embodiments is not intended to be limiting, and the appended claims should not be deemed to be limited by such statements. More generally, no language in the specification should be construed as indicating any non-claimed element as being essential to the practice of the invention. This invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contraindicated by context.

What is claimed is:

1. A conjugate comprising at least one charged highly branched polymeric dendrimer having conjugated thereto both: a) at least one T helper peptide that specifically binds to a professional antigen presenting cell and; b) at least one nucleic acid molecule comprising a sequence encoding at least one antigen, wherein the at least one T helper peptide is a Pan-DR epitope (PADRE).

2. The conjugate of claim 1, wherein the at least one T helper peptide comprises the amino acid sequence of any of SEQ ID NOs:1 and 2-24.

3. The conjugate of claim 1, wherein the nucleic acid molecule comprises an expression control sequence operably linked to the sequence encoding the at least one antigen.

4. The conjugate of claim 1, wherein the at least one antigen is a cancer antigen or an antigen from an infectious pathogen.

5. The conjugate of claim 1, wherein the at least one charged highly branched polymeric dendrimer is a Polyamidoamine (PAMAM) dendrimer.

6. A composition comprising the conjugate of claim 1, a pharmaceutically acceptable carrier and an oil and water emulsion.

7. The conjugate of claim 1, wherein the at least one charged highly branched polymeric dendrimer has further conjugated thereto a peptide comprising an antigen that is different from the at least one antigen.

8. A conjugate comprising at least one charged highly branched polymeric dendrimer having conjugated thereto both: a) at least one T helper peptide that specifically binds to a professional antigen presenting cell and; b) at least one iRNA, miRNA or siRNA or a nucleic acid molecule encoding at least one iRNA, miRNA or siRNA, wherein the at least one T helper peptide is a Pan-DR epitope (PADRE).

9. A conjugate comprising a positively-charged highly branched polymeric dendrimer having conjugated thereto both: a) at least one T helper peptide that specifically binds to a professional antigen presenting cell and; b) at least one nucleic acid encoding a polypeptide, wherein the at least one T helper peptide is a Pan-DR epitope (PADRE).

10. The conjugate of claim 1, wherein the at least one T helper peptide is covalently attached to functional groups on the surface of the at least one charged highly branched polymeric dendrimer.

11. The conjugate of claim 10, wherein the at least one T helper peptide comprises the amino acid sequence of any of SEQ ID NOs:1 and 2-24.

12. A method for eliciting an immune response comprising administering to a mammal or in vitro in cells from a mammal a composition comprising a conjugate comprising at least one charged highly branched polymeric dendrimer having conjugated thereto both: a) at least one T helper peptide that specifically binds to a professional antigen presenting cell and; b) at least one nucleic acid molecule comprising a sequence encoding at least one antigen, wherein administering the composition to the mammal elicits an immune response against the antigen, wherein the at least one T helper peptide is a Pan-DR epitope (PADRE).

13. A method of delivering a nucleic acid molecule into a cell comprising the steps of:
    (a) providing a composition comprising a conjugate comprising at least one charged highly branched polymeric dendrimer having conjugated thereto both: at least one T helper peptide and at least one nucleic acid molecule, wherein the at least one T helper peptide is a Pan-DR epitope (PADRE); and
    (b) contacting a cell with the composition such that the conjugate is internalized by the cell.

14. A method for eliciting an immune response comprising administering to a vertebrate or in vitro in cells from a vertebrate a composition comprising a conjugate comprising at least one charged highly branched polymeric dendrimer having conjugated thereto both: a) at least one T helper peptide that specifically binds to a professional antigen presenting cell and; b) at least one nucleic acid molecule comprising a sequence encoding at least one antigen, wherein administering the composition to the vertebrate elicits an immune response against the antigen, wherein the at least one T helper peptide is a Pan-DR epitope (PADRE).

* * * * *

```
                        SEQUENCE LISTING

<160> NUMBER OF SEQ ID NOS: 27

<210> SEQ ID NO 1
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (1)..(1)
<223> OTHER INFORMATION: D-alanine
<220> FEATURE:
<221> NAME/KEY: MOD_RES
<222> LOCATION: (3)..(3)
<223> OTHER INFORMATION: cyclohexylalanine
<220> FEATURE:
<221> NAME/KEY: MOD_RES
<222> LOCATION: (14)..(14)
<223> OTHER INFORMATION: D-alanine
<220> FEATURE:
<221> NAME/KEY: MOD_RES
<222> LOCATION: (15)..(15)
<223> OTHER INFORMATION: aminohexanoic acid

<400> SEQUENCE: 1

Ala Lys Xaa Val Ala Ala Trp Thr Leu Lys Ala Ala Ala Ala Xaa Cys
1               5                   10                  15

<210> SEQ ID NO 2
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-alanine
<220> FEATURE:
<221> NAME/KEY: MOD_RES
<222> LOCATION: (3)..(3)
<223> OTHER INFORMATION: cyclohexylalanine
<220> FEATURE:
<221> NAME/KEY: MOD_RES
<222> LOCATION: (13)..(13)
<223> OTHER INFORMATION: D-alanine

<400> SEQUENCE: 2

Ala Lys Xaa Val Ala Ala Trp Thr Leu Lys Ala Ala Ala
1               5                   10

<210> SEQ ID NO 3
<211> LENGTH: 13
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-alanine
<220> FEATURE:
<221> NAME/KEY: MOD_RES
<222> LOCATION: (13)..(13)
<223> OTHER INFORMATION: D-alanine

<400> SEQUENCE: 3

Ala Lys Phe Val Ala Ala Trp Thr Leu Lys Ala Ala Ala
1               5                   10

<210> SEQ ID NO 4
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-alanine
<220> FEATURE:
<221> NAME/KEY: MOD_RES
<222> LOCATION: (13)..(13)
<223> OTHER INFORMATION: D-alanine

<400> SEQUENCE: 4

Ala Lys Tyr Val Ala Ala Trp Thr Leu Lys Ala Ala Ala
1               5                   10

<210> SEQ ID NO 5
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-alanine
<220> FEATURE:
<221> NAME/KEY: MOD_RES
<222> LOCATION: (13)..(13)
<223> OTHER INFORMATION: D-alanine

<400> SEQUENCE: 5

Ala Lys Phe Val Ala Ala Tyr Thr Leu Lys Ala Ala Ala
1               5                   10

<210> SEQ ID NO 6
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-alanine
<220> FEATURE:
<221> NAME/KEY: MOD_RES
<222> LOCATION: (3)..(3)
<223> OTHER INFORMATION: cyclohexylalanine
```

```
<220> FEATURE:
<221> NAME/KEY: MOD_RES
<222> LOCATION: (13)..(13)
<223> OTHER INFORMATION: D-alanine

<400> SEQUENCE: 6

Ala Lys Xaa Val Ala Ala Tyr Thr Leu Lys Ala Ala Ala
1               5                   10

<210> SEQ ID NO 7
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-alanine
<220> FEATURE:
<221> NAME/KEY: MOD_RES
<222> LOCATION: (13)..(13)
<223> OTHER INFORMATION: D-alanine

<400> SEQUENCE: 7

Ala Lys Tyr Val Ala Ala Tyr Thr Leu Lys Ala Ala Ala
1               5                   10

<210> SEQ ID NO 8
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-alanine
<220> FEATURE:
<221> NAME/KEY: MOD_RES
<222> LOCATION: (13)..(13)
<223> OTHER INFORMATION: D-alanine

<400> SEQUENCE: 8

Ala Lys Phe Val Ala Ala His Thr Leu Lys Ala Ala Ala
1               5                   10

<210> SEQ ID NO 9
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-alanine
<220> FEATURE:
<221> NAME/KEY: MOD_RES
<222> LOCATION: (3)..(3)
<223> OTHER INFORMATION: cyclohexylalanine
<220> FEATURE:
<221> NAME/KEY: MOD_RES
<222> LOCATION: (13)..(13)
<223> OTHER INFORMATION: D-alanine

<400> SEQUENCE: 9

Ala Lys Xaa Val Ala Ala His Thr Leu Lys Ala Ala Ala
1               5                   10
```

```
<210> SEQ ID NO 10
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-alanine
<220> FEATURE:
<221> NAME/KEY: MOD_RES
<222> LOCATION: (13)..(13)
<223> OTHER INFORMATION: D-alanine

<400> SEQUENCE: 10

Ala Lys Tyr Val Ala Ala His Thr Leu Lys Ala Ala Ala
1               5                   10

<210> SEQ ID NO 11
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-alanine
<220> FEATURE:
<221> NAME/KEY: MOD_RES
<222> LOCATION: (13)..(13)
<223> OTHER INFORMATION: D-alanine

<400> SEQUENCE: 11

Ala Lys Phe Val Ala Ala Asn Thr Leu Lys Ala Ala Ala
1               5                   10

<210> SEQ ID NO 12
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-alanine
<220> FEATURE:
<221> NAME/KEY: MOD_RES
<222> LOCATION: (3)..(3)
<223> OTHER INFORMATION: cyclohexylalanine
<220> FEATURE:
<221> NAME/KEY: MOD_RES
<222> LOCATION: (13)..(13)
<223> OTHER INFORMATION: D-alanine

<400> SEQUENCE: 12

Ala Lys Xaa Val Ala Ala Asn Thr Leu Lys Ala Ala Ala
1               5                   10

<210> SEQ ID NO 13
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (1)..(1)
<223> OTHER INFORMATION: D-alanine
<220> FEATURE:
<221> NAME/KEY: MOD_RES
<222> LOCATION: (13)..(13)
<223> OTHER INFORMATION: D-alanine

<400> SEQUENCE: 13

Ala Lys Tyr Val Ala Ala Asn Thr Leu Lys Ala Ala Ala
1               5                   10

<210> SEQ ID NO 14
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Ala Lys Phe Val Ala Ala Trp Thr Leu Lys Ala Ala Ala
1               5                   10

<210> SEQ ID NO 15
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Ala Lys Tyr Val Ala Ala Trp Thr Leu Lys Ala Ala Ala
1               5                   10

<210> SEQ ID NO 16
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Ala Lys Phe Val Ala Ala Tyr Thr Leu Lys Ala Ala Ala
1               5                   10

<210> SEQ ID NO 17
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: cyclohexylalanine

<400> SEQUENCE: 17

Ala Lys Xaa Val Ala Ala Tyr Thr Leu Lys Ala Ala Ala
1               5                   10

<210> SEQ ID NO 18
<211> LENGTH: 13
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 18

Ala Lys Tyr Val Ala Ala Tyr Thr Leu Lys Ala Ala Ala
1               5                   10

<210> SEQ ID NO 19
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Ala Lys Phe Val Ala Ala His Thr Leu Lys Ala Ala Ala
1               5                   10

<210> SEQ ID NO 20
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: cyclohexylalanine

<400> SEQUENCE: 20

Ala Lys Xaa Val Ala Ala His Thr Leu Lys Ala Ala Ala
1               5                   10

<210> SEQ ID NO 21
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Ala Lys Tyr Val Ala Ala His Thr Leu Lys Ala Ala Ala
1               5                   10

<210> SEQ ID NO 22
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Ala Lys Phe Val Ala Ala Asn Thr Leu Lys Ala Ala Ala
1               5                   10

<210> SEQ ID NO 23
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
```

```
<222> LOCATION: (3)..(3)
<223> OTHER INFORMATION: cyclohexylalanine

<400> SEQUENCE: 23

Ala Lys Xaa Val Ala Ala Asn Thr Leu Lys Ala Ala Ala
1               5                   10

<210> SEQ ID NO 24
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Ala Lys Tyr Val Ala Ala Asn Thr Leu Lys Ala Ala Ala
1               5                   10

<210> SEQ ID NO 25
<211> LENGTH: 11
<212> TYPE: PRT
<213> ORGANISM: Unknown
<220> FEATURE:
<223> OTHER INFORMATION: Description of Unknown: Provirus PR8 virus

<400> SEQUENCE: 25

Ser Phe Glu Arg Phe Glu Ile Phe Pro Lys Glu
1               5                   10

<210> SEQ ID NO 26
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: cyclohexylalanine

<400> SEQUENCE: 26

Ala Lys Xaa Val Ala Ala Trp Thr Leu Lys Ala Ala Ala
1               5                   10

<210> SEQ ID NO 27
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Gly Ser Gly Gly Gly Gly Ser
1               5
```